(12) United States Patent
Ohashi et al.

(10) Patent No.: US 11,581,478 B2
(45) Date of Patent: Feb. 14, 2023

(54) MOUNTING STRUCTURE, ULTRASONIC DEVICE, ULTRASONIC PROBE, ULTRASONIC APPARATUS, AND ELECTRONIC APPARATUS

(71) Applicant: Seiko Epson Corporation, Tokyo (JP)

(72) Inventors: Koji Ohashi, Matsumoto (JP); Chikara Kojima, Matsumoto (JP); Hiroshi Matsuda, Chino (JP); Hironori Suzuki, Chino (JP); Shuichi Tanaka, Chino (JP)

(73) Assignee: SEIKO EPSON CORPORATION ( * ) Notice: Subject to any disclaimer, the term of this patent is extended or adjusted under 35 U.S.C. 154(b) by 1147 days.

(21) Appl. No.: 16/097,011

(22) PCT Filed: Apr. 20, 2017

(86) PCT No.: PCT/JP2017/015920
§ 371 (c)(1),
(2) Date: Oct. 26, 2018

(87) PCT Pub. No.: WO2017/188125
PCT Pub. Date: Nov. 2, 2017

(65) Prior Publication Data
US 2019/0131515 A1 May 2, 2019

(30) Foreign Application Priority Data
Apr. 27, 2016 (JP) .............. JP2016-089569
Sep. 21, 2016 (JP) .............. JP2016-184369

(51) Int. Cl.
H01L 41/053 (2006.01)
H01L 41/047 (2006.01)
(Continued)

(52) U.S. Cl.
CPC .......... *H01L 41/053* (2013.01); *B06B 1/0622* (2013.01); *B06B 1/0629* (2013.01);
(Continued)

(58) Field of Classification Search
CPC ... H01L 41/053; H01L 41/047; B06B 1/0622; B06B 1/0629
(Continued)

(56) References Cited

U.S. PATENT DOCUMENTS 6,576,499 B2 6/2003 Funaya et al.
2005/0062153 A1 3/2005 Saito et al.
(Continued)

FOREIGN PATENT DOCUMENTS

CN 1584672 A 2/2005
JP 2001-168265 A 6/2001
(Continued)

*Primary Examiner* — Derek J Rosenau
(74) *Attorney, Agent, or Firm* — Harness, Dickey & Pierce, P.L.C.

(57) ABSTRACT

A mounting structure includes: a first substrate that has a first surface on which a functional element is provided; a wiring portion that is provided at a position, which is different from a position of the functional element on the first surface, and is conductively connected to the functional element; a second substrate that has a second surface that is opposite to the first surface; and a conduction portion that is provided on the second surface, is connected to the wiring portion, and is conductively connected the functional element. The shortest distance between the functional element and the second substrate is longer than the longest distance between the second substrate and a position where the wiring portion is connected to the conduction portion.

16 Claims, 26 Drawing Sheets

(51) Int. Cl.
*B06B 1/06* (2006.01)
*A61B 8/00* (2006.01)
*H01L 27/20* (2006.01)

(52) U.S. Cl.
CPC ........ *H01L 41/047* (2013.01); *H01L 41/0475* (2013.01); *A61B 8/4444* (2013.01); *A61B 8/4477* (2013.01); *A61B 8/4494* (2013.01); *H01L 27/20* (2013.01)

(58) Field of Classification Search
USPC .............................. 310/322, 334, 335, 348
See application file for complete search history.

(56) References Cited

U.S. PATENT DOCUMENTS

| | | | |
|---|---|---|---|
| 2007/0108627 | A1 | 5/2007 | Kozaka et al. |
| 2008/0116765 | A1* | 5/2008 | Sugiura ................. B06B 1/0629 310/334 |

FOREIGN PATENT DOCUMENTS

| | | |
|---|---|---|
| JP | 2006-094459 A | 4/2006 |
| JP | 2007-141970 A | 6/2007 |
| JP | 2007-180166 A | 7/2007 |
| JP | 2010-287836 A | 12/2010 |
| JP | 2011-035296 A | 2/2011 |
| JP | 2013-030789 A | 2/2013 |
| JP | 2013-153102 A | 8/2013 |

\* cited by examiner

MOUNTING STRUCTURE, ULTRASONIC DEVICE, ULTRASONIC PROBE, ULTRASONIC APPARATUS, AND ELECTRONIC APPARATUS

CROSS-REFERENCE TO RELATED APPLICATIONS

This application is a U.S. National Stage Application of International Application No. PCT/JP2017/015920, filed on Apr. 20, 2017, and published in Japanese as WO 2017/188125 A1 on Nov. 2, 2017, which claims priority to Japanese Patent Application Nos. 2016-184369, filed on Sep. 21, 2016 and 2016-089569, filed on Apr. 27, 2016. The entire disclosures of the above applications are incorporated herein by reference.

BACKGROUND

Technical Field

The present invention relates to a mounting structure, an ultrasonic device, an ultrasonic probe, an ultrasonic apparatus, and an electronic apparatus.

Related Art

In a case where an electric component is mounted on a circuit substrate, there is a mounting method in which a wiring on the circuit substrate side is electrically connected to a wiring on the electric component side via a bump electrode (for example, refer to JP-2007-180166).

JP-2007-180166 discloses the electric component in which an electronic element such as an IC chip and a conductive film as a metal wiring connected to the electronic element are formed on a substrate. A part of the conductive film is provided on a surface of a resin protrusion formed at a peripheral edge portion of the substrate, and the bump electrode is configured to have the part of the conductive film and the resin protrusion. The circuit substrate is a substrate on which a liquid crystal panel is formed, and an electrode terminal is formed outside a region in which liquid crystal is disposed. The electric component is bonded to the circuit substrate in a state in which the bump electrodes on the electric component side are brought into direct contact with the electrode terminals on the circuit substrate side.

However, in the configuration disclosed in JP-2007-180166, the electrode terminal of the circuit substrate is formed outside the region in which a functional element such as liquid crystal is formed, and the bump electrode of the electronic component is formed at the peripheral edge portion of the substrate. The electrode terminal is brought into contact with the bump electrode, and thus wiring connection between the circuit substrate and the electronic component is performed at a position separated from the functional element.

However, in the above-described wiring method, in a case where wiring connection is performed in the region in which the functional element is formed, alignment between the circuit substrate and the electronic component is required to be performed with high accuracy. In other words, in a case where the alignment accuracy is not sufficient, there is concern that the bump electrode may interfere with the functional element. As mentioned above, in the configuration of the related art, it is not easy to perform electrical connection between substrates in the region in which the functional element is formed.

An object of the present invention is to provide a mounting structure, an ultrasonic device, an ultrasonic probe, an ultrasonic apparatus, and an electronic apparatus as application examples and embodiments, capable of easily performing electrical connection between substrates.

SUMMARY

A mounting structure according to an application example includes: a first substrate that has a first surface on which a functional element is provided; a wiring portion that is provided at a position, which is different from a position of the functional element on the first surface, and is conductively connected to the functional element; a second substrate that has a second surface that is opposite to the first surface; and a conduction portion that is provided on the second surface, is connected to the wiring portion, and is conductively connected the functional element. The shortest distance between the functional element and the second substrate is longer than the longest distance between the second substrate and a position where the wiring portion is connected to the conduction portion.

In the application example, the functional element and the wiring portion conductively connected to the functional element are provided on the first surface of the first substrate. The conduction portion connected to the wiring portion is provided on the second surface of the second substrate. The shortest distance between the functional element and the second substrate is longer than the longest distance between the second substrate and the position where the wiring portion is connected to the conduction portion. In this configuration, for example, even if a position difference occurs in the conduction portion when wiring connection is performed around the functional element, it is possible to suppress interference between the conduction portion and the functional element. Therefore, it is possible to easily perform wiring connection between the first substrate and the second substrate.

In the mounting structure according to the application example, it is preferable that an area of a region in which the conduction portion is bonded to the second substrate is larger than an area of a region in which the wiring portion is connected to the conduction portion.

In the application example, the area of the region in which the conduction portion is bonded to the second substrate is larger than the area of the region in which the wiring portion is connected to the conduction portion. In other words, a sectional area of the conduction portion in a plane intersecting the first direction is reduced from the second substrate toward the first substrate. In this configuration, a distance between the conduction portion and the functional element in the plane intersecting the first direction can be increased from the first substrate toward the second substrate on which the functional element is provided. Therefore, it is possible to further suppress interference between the conduction portion and the functional element. The conduction portion and the functional element can be disposed to be closer to each other in plan view viewed from the first direction.

In the mounting structure according to the application example, it is preferable that at least one of the wiring portion and the conduction portion includes a resin part and a conductive part covering the resin part.

In the application example, at least one of the wiring portion and the conduction portion includes the resin part and the conductive part covering the resin part. In this configuration, when the conduction portion is brought into contact with the wiring portion, the resin part can be elastically deformed, and one of the wiring portion and the conduction portion can be deformed along the other thereof. Therefore, it is possible to improve close contact between the conduction portion and the wiring portion, and thus it is possible to improve connection reliability.

In the mounting structure according to the application example, it is preferable that in a first direction directed from the first substrate to the second substrate, a thickness of the resin part at a position overlapping a connection region between the conduction portion and the wiring portion is larger than a thickness of the conductive part.

In the application example, the thickness of the resin part is larger than the thickness of the conductive part in the connection region between the conduction portion and the wiring portion. The resin part is thicker than the conductive part as mentioned above, and thus the conduction portion can be easily deformed. Consequently, the stress of when the wiring portion is brought into contact with the conduction portion can be alleviated, and thus it is possible to suppress the occurrence of strain of the first substrate and the second substrate. Since a thickness of the conductive part is small, and thus the resin part is easily deformed, for example, even if an error occurs in a thickness of the wiring portion, the wiring portion can be brought into close contact with the conduction portion due to deformation of the resin part, and thus it is possible to improve the connection reliability.

In the mounting structure according to the application example, it is preferable that the resin part has a substantially hemispherical shape protruding from the second surface in a case where the conduction portion is not elastically deformed, and, if the maximum diameter of an end surface of the resin part on the second substrate side is indicated by L, a distance d from the second substrate to the functional element satisfies a relationship of d>L/2.

In the application example, the resin part has the substantially hemispherical shape protruding from the second surface in a state of not being elastically deformed. If the maximum diameter (that is, a diameter) of the end surface of the resin part on the second substrate side is indicated by L, the distance d from the second substrate to the functional element satisfies the relationship of d>L/2. In other words, the distance d is larger than a radius of the resin part before being elastically deformed.

In this configuration, the conduction portion is elastically deformed, and thus the maximum value of a distance between a tip end thereof and the second substrate is about L/2 (that is, the radius of the resin part). Therefore, the distance d from the second substrate to the functional element is made larger than L/2, and thus it is possible to further suppress interference between the conduction portion and the functional element.

The conduction portion may be formed by forming the resin part by heating, melting, and then solidifying a resin, and by coating the resin part with the conductive part.

In the mounting structure according to the application example, it is preferable that the wiring portion and the conduction portion intersect each other in plan view in a first direction directed from the first substrate to the second substrate.

In the application example, the wiring portion and the conduction portion intersect each other in the plan view. Consequently, a position difference between the first substrate and the second substrate is allowable in a plane intersecting the first direction during wiring connection, and thus it is possible to prevent defective connection from occurring. In other words, in the application example, it is possible to increase an allowable amount for a position difference, compared with a case where the wiring portion and the conduction portion do not intersect each other (for example, a case where the wiring portion and the conduction portion are parallel to each other or have point connection) in the plan view. Thus, alignment between the first substrate and the second substrate can be easily performed, and wiring connection can also be easily performed. It is possible to improve connection reliability.

In the mounting structure according to the application example, it is preferable that at least one of the wiring portion and the conduction portion includes a resin part and a conductive part covering at least a part of the resin part.

In the application example, at least one of the conduction portion and the wiring portion includes the resin part and the conductive part covering the resin part. In this configuration, when the conduction portion is brought into contact with the wiring portion, the resin part can be elastically deformed, and one of the wiring portion and the conduction portion can be deformed along the other thereof. Therefore, it is possible to improve close contact between the conduction portion and the wiring portion, and thus it is possible to improve connection reliability.

In the mounting structure according to the application example, it is preferable that one of the wiring portion and the conduction portion has a second direction, which is parallel to the first surface, as a longitudinal direction, the other of the wiring portion and the conduction portion has a third direction, which is parallel to the first surface and intersects with the second direction, as a longitudinal direction, and, in the second direction, a dimension of the conductive part is larger than a dimension of the other of the wiring portion and the conduction portion.

In the application example, one of the conduction portion has the second direction as the longitudinal direction, and the other thereof has the third direction as the longitudinal direction. In the second direction, a dimension of the conductive part is larger than a dimension of the other of the wiring portion and the conduction portion. Consequently, it is possible to maintain connection reliability on the basis of the elastic force while allowing a position difference between the first substrate and the second substrate in the second direction during wiring connection in the second direction.

In the mounting structure according to the application example, it is preferable that the conduction portion has the resin part and a conductive part covering the resin part, the first substrate is provided with an extraction wiring that is connected to the functional element and is smaller than the wiring portion in a thickness in the first direction directed from the first substrate to the second substrate, the mounting structure further including: a second conduction portion that is connected to the extraction wiring; a second resin part which is larger than the resin part in a thickness in the first direction directed from the first substrate to the second substrate; and a second conductive part, which covers the second resin part.

In the application example, the conduction portion has a configuration in which the resin part is covered with the conductive part. The second conduction portion has a configuration in which the second resin part larger than the second conductive part in thickness is covered with the second conductive part. The second conduction portion is brought into contact with and is connected to the extraction wiring smaller than the wiring portion in dimension in the first direction. Here, the second conduction portion is larger than the conduction portion in thickness in the first direction directed from the first substrate to the second substrate.

Therefore, in a case of the same deformation amount in the first direction during the connection, a contact area between the second conduction portion and the extraction wiring may be larger than a contact area between the conduction portion and the wiring portion. Further, it is possible to reduce the contact resistance, and thus it is possible to increase a current amount. As mentioned above, the extraction wiring is provided to be smaller than the wiring portion in dimension, and thereby it is possible to perform the wiring connection using the second conduction portion larger than the conduction portion, and thus it is possible to reduce the contact resistance.

In the mounting structure according to the application example, it is preferable that the wiring portion is made of a metal material, and a ratio of a height of the first surface in a normal direction to a width of the first surface in a surface direction is 0.1 or more and 5 or less.

In the application example, in the wiring portion, the ratio (aspect ratio) of the height of the first surface in the normal direction to the width of the first surface in the surface direction is 0.1 or more and 5 or less. Consequently, it is possible to prevent the wiring portion from being deformed when force is applied from the conduction portion, and thus it is possible to improve the reliability of electrical connection.

In the mounting structure according to the application example, it is preferable that the functional element includes a vibrator that vibrates along a first direction directed from the first substrate to the second substrate.

In the application example, the functional element is configured to include the vibrator. Also in this configuration, as described above, it is possible to suppress interference between the conduction portion and the functional element. In other words, it is possible to prevent the conduction portion from hindering vibration of the vibrator, and thus it is possible to appropriately drive the vibrator.

In the mounting structure according to the application example, it is preferable that a connection position between the wiring portion and the conduction portion is located further toward the second substrate side than a vibration range of the vibrator in the first direction.

In the application example, a connection position between the wiring portion and the conduction portion is located further toward the second substrate side than a vibration range of the vibrator provided on the first substrate. In this configuration, the conduction portion can be disposed outside the drive range of the vibrator. Consequently, it is possible to further prevent the conduction portion from hindering vibration of the vibrator, and thus it is possible to appropriately drive the vibrator.

In the mounting structure according to the application example, it is preferable that the functional element is an ultrasonic transducer including a flexible film formed on the first substrate, and the vibrator provided on the flexible film.

In the application example, the functional element is the ultrasonic transducer that is configured to include the flexible film and the vibrator. In this configuration, as described above, it is possible to prevent the conduction portion from hindering vibration of the vibrator, and thus it is possible to appropriately drive the ultrasonic transducer.

It is preferable that the mounting structure according to the application example further includes a bonding portion that bonds the first substrate to the second substrate, the first substrate has a functional region in which a plurality of the functional elements are formed, and the bonding portion bonds the first substrate to the second substrate in the functional region.

In the application example, the bonding portion bonds the first substrate to the second substrate in the functional region in which the functional element is formed.

Consequently, for example, even in a case where a plurality of conduction portions and wiring portions are provided in the functional region, that is, a plurality of connection positions are present, the uniformity of a distance between the first substrate and the second substrate in the functional region can be improved, and thus the connection reliability at each connection position can be improved.

An ultrasonic device according to an application example includes: a first substrate that has a first surface on which a vibrator is provided; a wiring portion that is provided at a position, which is different from a position of the vibrator on the first surface, and is conductively connected to the vibrator; a second substrate that has a second surface that is opposite to the first surface; and a conduction portion that is provided on the second surface, is connected to the wiring portion, and is conductively connected to the vibrator. The shortest distance between the vibrator and the second substrate is longer than the longest distance between the second substrate and a position where the wiring portion is connected to the conduction portion.

In the application example, the vibrator and the wiring portion and the conduction portion, which are conductively connected to the vibrator, are provided on the first surface of the first substrate. The conduction portion connected to the wiring portion is provided on the second surface of the second substrate. The shortest distance between the vibrator and the second substrate is longer than the longest distance between the second substrate and the position where the wiring portion is connected to the conduction portion. In this configuration, similar to the application example, it is possible to suppress interference between the conduction portion and the vibrator, it is possible to easily perform wiring connection between the first substrate and the second substrate, and also it is possible to easily manufacture an ultrasonic device.

An ultrasonic probe according to an application example includes: a first substrate that has a first surface on which a vibrator is provided; a wiring portion that is provided at a position, which is different from a position of the vibrator on the first surface, and is conductively connected to the vibrator; a second substrate that has a second surface that is opposite to the first surface; a conduction portion that is provided on the second surface, is connected to the wiring portion, and is conductively connected the vibrator; and a case in which the first substrate, the wiring portion, the second substrate, and the conduction portion are stored. The shortest distance between the vibrator and the second substrate is longer than the longest distance between the second substrate and a position where the wiring portion is connected to the conduction portion.

In the application example, the vibrator and the wiring portion and the conduction portion, which are conductively connected to the vibrator, are provided on the first surface of the first substrate. The conduction portion connected to the wiring portion is provided on the second surface of the second substrate. The shortest distance between the vibrator and the second substrate is longer than the longest distance between the second substrate and the position where the wiring portion is connected to the conduction portion. In this configuration, similar to the application example, it is possible to suppress interference between the conduction portion and the vibrator, it is possible to easily perform wiring connection between the first substrate and the second substrate, and also it is possible to easily manufacture an ultrasonic probe.

An ultrasonic apparatus according to an application example includes: a first substrate that has a first surface on which a vibrator is provided; a wiring portion that is provided at a position, which is different from a position of the vibrator on the first surface, and is connected to the vibrator; a second substrate that has a second surface that is opposite to the first surface; a conduction portion that is provided on the second surface, is connected to the wiring portion, and is conductively connected to the vibrator; and a controller that controls the vibrator. The shortest distance between the vibrator and the second substrate is longer than the longest distance between the second substrate and a position where the wiring portion is connected to the conduction portion.

In the application example, the vibrator and the wiring portion and the conduction portion, which are conductively connected to the vibrator, are provided on the first surface of the first substrate. The conduction portion connected to the wiring portion is provided on the second surface of the second substrate. The shortest distance between the vibrator and the second substrate is longer than the longest distance between the second substrate and the position where the wiring portion is connected to the conduction portion. In this configuration, similar to the application example, it is possible to suppress interference between the conduction portion and the vibrator, it is possible to easily perform wiring connection between the first substrate and the second substrate, and also it is possible to easily manufacture an ultrasonic apparatus.

An electronic apparatus according to an application example includes: a first substrate that has a first surface on which a functional element is provided; a wiring portion that is provided at a position, which is different from a position of the functional element on the first surface, and is conductively connected to the functional element; a second substrate that has a second surface that is opposite to the first surface; and a conduction portion that is provided on the second surface, is connected to the wiring portion, and is conductively connected to the functional element; and a controller that controls the functional element. The shortest distance between the functional element and the second substrate is longer than the longest distance between the second substrate and a position where the wiring portion is connected to the conduction portion.

In the application example, the functional element and the wiring portion and the conduction portion, which are conductively connected to the functional element, are provided on the first surface of the first substrate. The conduction portion connected to the wiring portion is provided on the second surface of the second substrate. The shortest distance between the functional element and the second substrate is longer than the longest distance between the second substrate and the position where the wiring portion is connected to the conduction portion. In this configuration, similar to the application example, it is possible to suppress interference between the conduction portion and the functional element, it is possible to easily perform wiring connection between the first substrate and the second substrate, and also it is possible to easily manufacture an ultrasonic apparatus.

DETAILED DESCRIPTION

First Embodiment

Hereinafter, a description will be made of an ultrasonic measuring apparatus according to a first embodiment of an ultrasonic apparatus with reference to the drawings.

Figure 1:
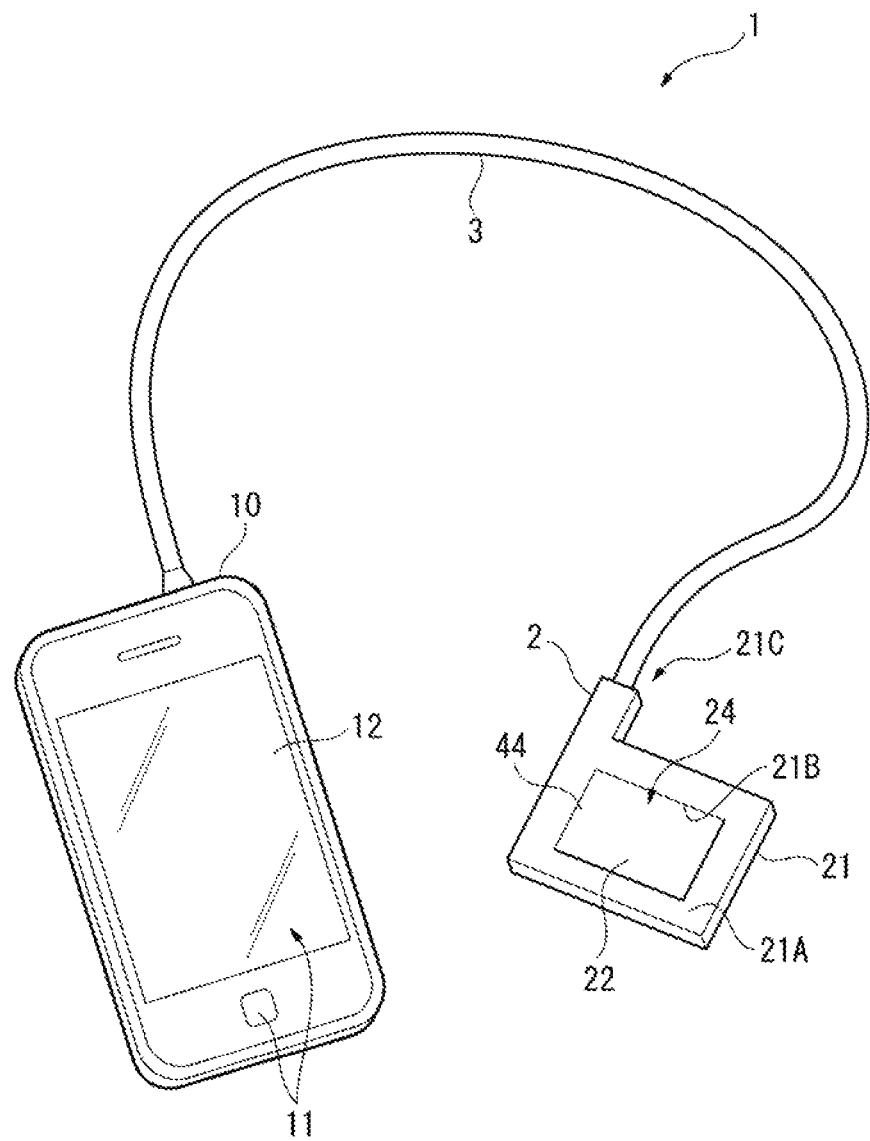
FIG. 1 is a perspective view showing a schematic configuration of an ultrasonic apparatus according to a first embodiment.
Figure 2:
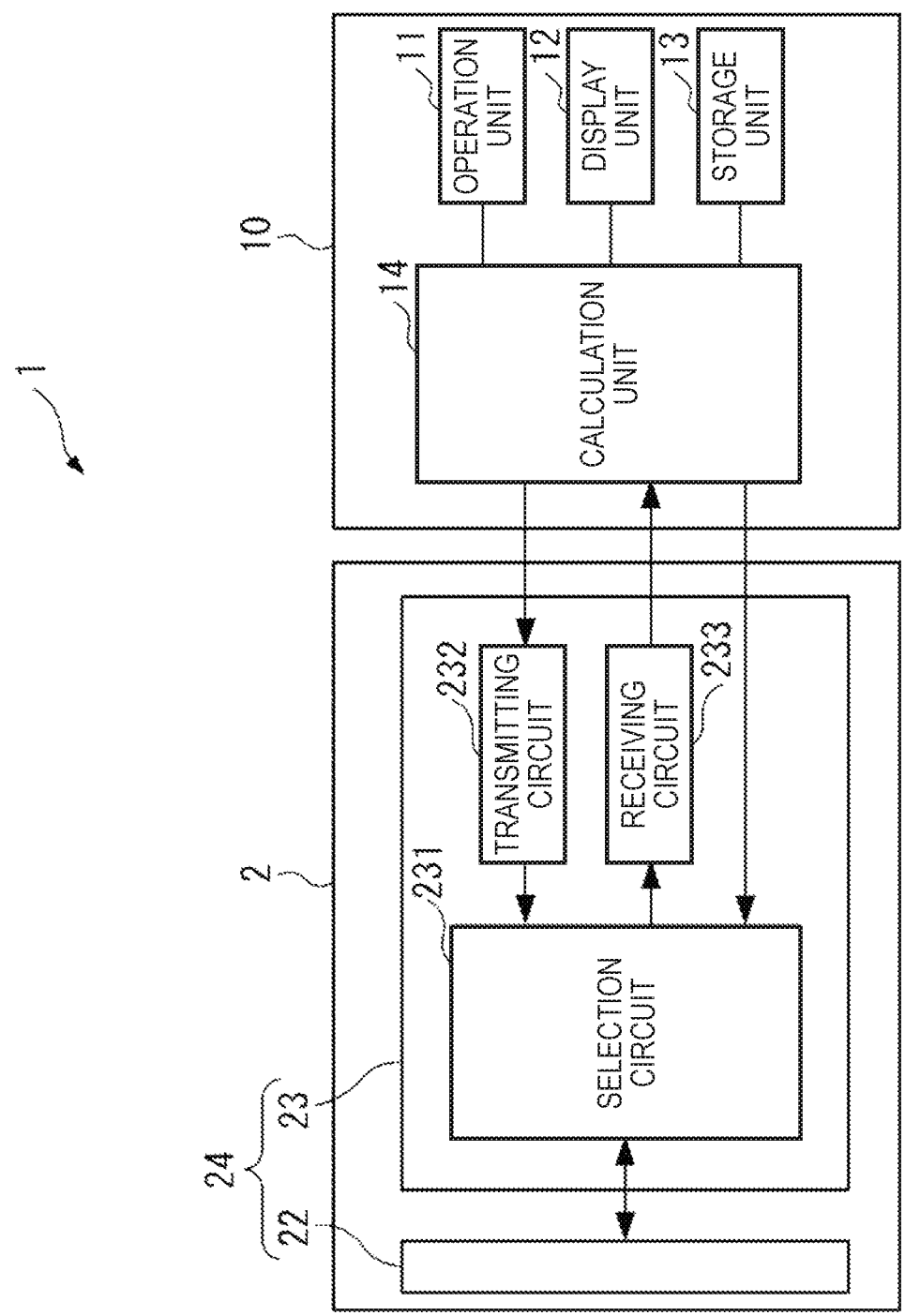
FIG. 2 is a block diagram showing a schematic configuration of the ultrasonic apparatus according to the first embodiment.

FIG. 1 is a perspective view showing a schematic configuration of an ultrasonic measuring apparatus 1 of the embodiment. FIG. 2 is a block diagram showing a schematic configuration of the ultrasonic measuring apparatus 1.

As shown in FIG. 1, the ultrasonic measuring apparatus 1 of the embodiment includes an ultrasonic probe 2 and a control device 10 that is electrically connected to the ultrasonic probe 2 via a cable 3.

In the ultrasonic measuring apparatus 1, the ultrasonic probe 2 is brought into close contact with a surface of a living body (for example, a human body), and an ultrasonic wave is transmitted into the living body from the ultrasonic probe 2. An ultrasonic wave reflected at an organ of the living body is received by the ultrasonic probe 2, and, for example, an internal tomographic image of the living body is acquired, or a state (for example, a blood flow) of an organ of the living body is measured, on the basis of received signals.

Configuration of Ultrasonic Probe

The ultrasonic probe 2 corresponds to an ultrasonic probe and includes a case 21, an ultrasonic device 22 stored in the case 21, and a circuit substrate 23 (refer to FIG. 2) provided with a driver circuit and the like for controlling the ultrasonic device 22. An ultrasonic sensor 24 is formed of the ultrasonic device 22 and the circuit substrate 23, and the ultrasonic sensor 24 forms an ultrasonic module.

Configuration of Case

As shown in FIG. 1, the case 21 is formed, for example, in a rectangular box shape in plan view, and a sensor window 21B is provided on one surface (sensor surface 21A) which is orthogonal to a thickness direction, and a part of the ultrasonic device 22 is exposed. A passing hole 21C of the cable 3 is provided at a part of the case 21 (a side surface in the example shown in FIG. 1), and the cable 3 is connected to the circuit substrate 23 inside the case 21 through the passing hole 21C. A gap between the cable 3 and the passing hole 21C is filled with, for example, a resin material, and thus water resistance is ensured.

In the embodiment, a configuration example in which the ultrasonic probe 2 and the control device 10 are connected to each other via the cable 3 is described, but, this is only an example, and, for example, the ultrasonic probe 2 and the control device 10 may be connected to each other through wireless communication, and various constituent elements of the control device 10 may be provided in the ultrasonic probe 2.

Configuration of Ultrasonic Device

Figure 3:
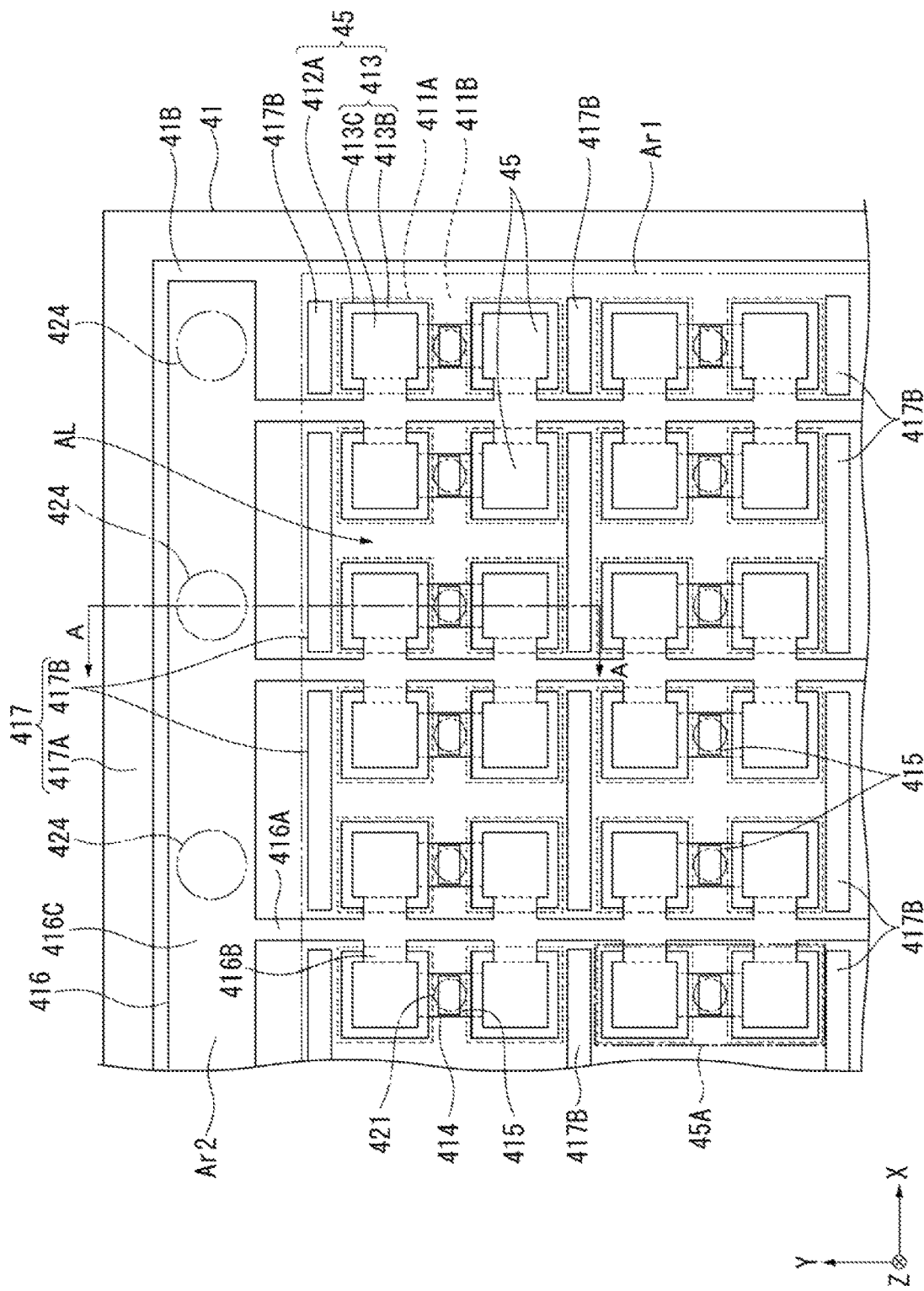
FIG. 3 is a plan view showing a schematic configuration of an element substrate in an ultrasonic device according to the first embodiment.
Figure 4:
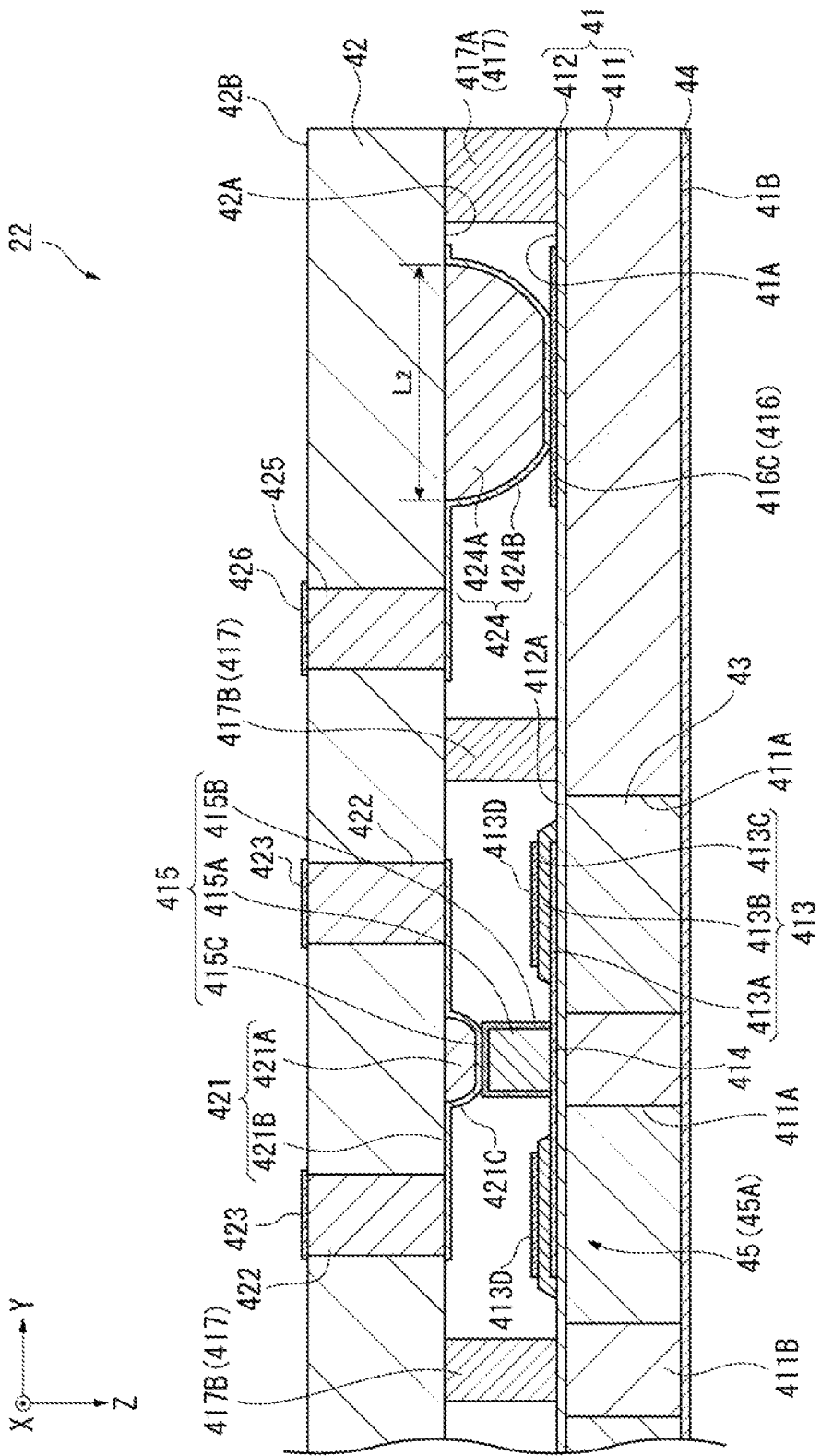
FIG. 4 is a sectional view of the ultrasonic device taken along the line A-A in FIG. 3.
Figure 5:
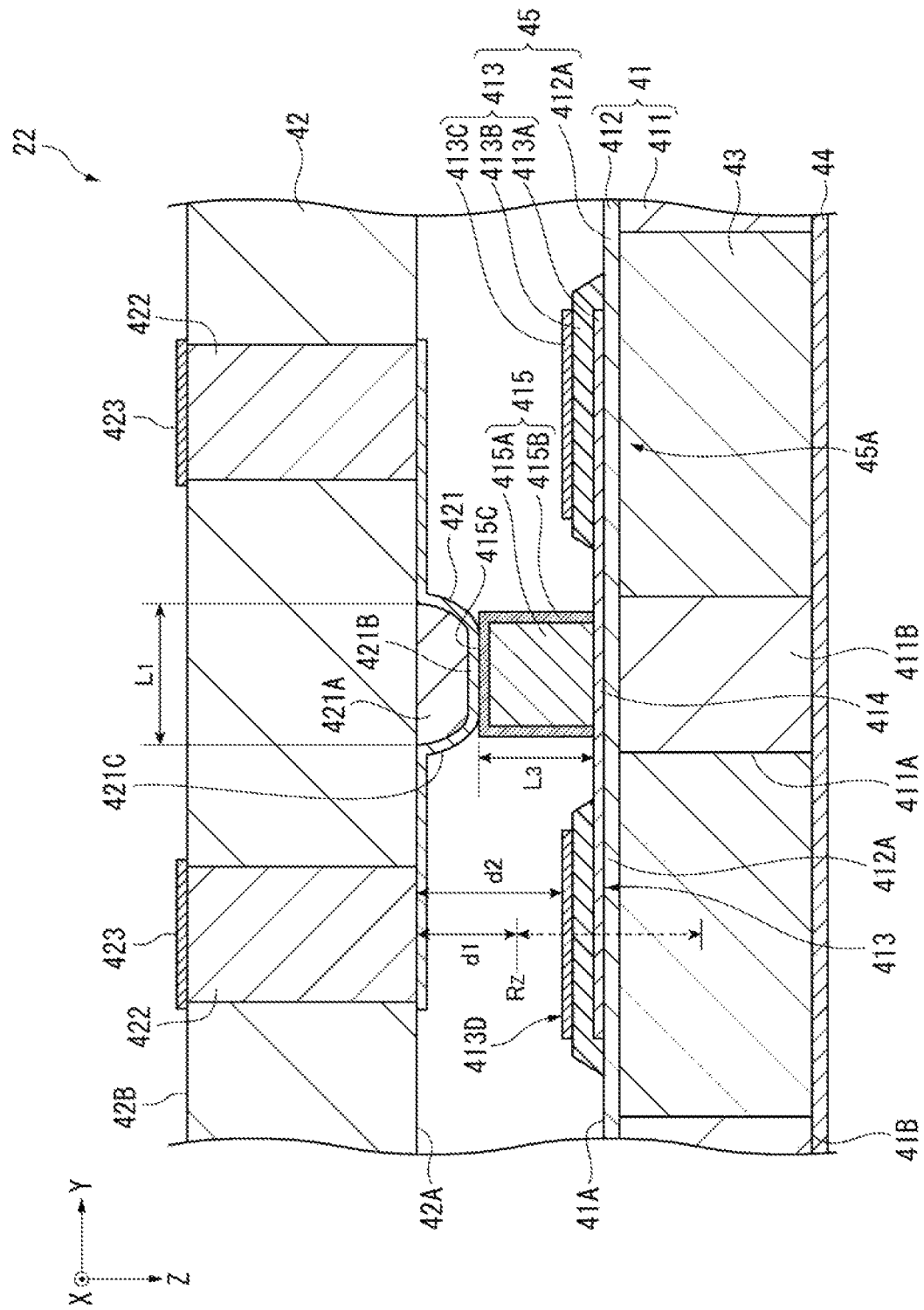
FIG. 5 is a sectional view showing a schematic configuration of main portions of the ultrasonic device according to the first embodiment.
Figure 6:
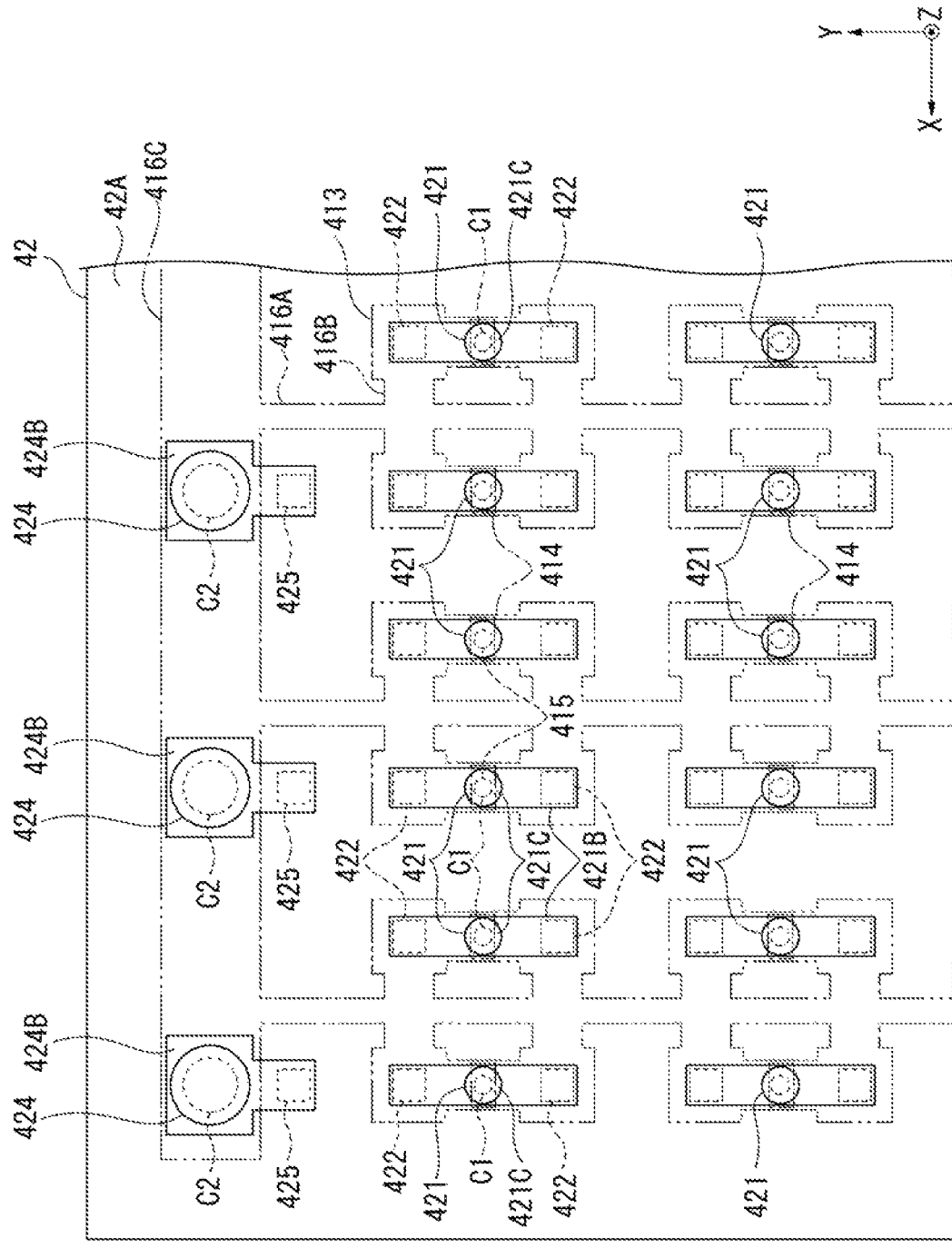
FIG. 6 is a plan view showing a schematic configuration of a sealing plate in the ultrasonic device according to the first embodiment.

FIG. 3 is a plan view in which an element substrate 41 of the ultrasonic device 22 is viewed from a protective film 44 side. FIG. 4 is a sectional view of the ultrasonic device 22 taken along the line A-A in FIG. 3. FIG. 5 is a sectional view showing a schematic configuration of the periphery of a first conduction portion 421 which will be described below in the ultrasonic device 22. FIG. 6 is a plan view schematically showing an ultrasonic transducer 45 viewed from the protective film 44 side.

As shown in FIG. 4, the ultrasonic device 22 is configured to include the element substrate 41, a sealing plate 42, an acoustic matching layer 43, and the protective film 44. As shown in FIG. 4, the element substrate 41 and the sealing plate 42 of the members are electrically connected to each other via the first conduction portion 421 provided on the sealing plate 42 side and a second conduction portion 424.

As shown in FIG. 3, the element substrate 41 is provided with a plurality of ultrasonic transducers 45 which transmit and receive an ultrasonic wave and are disposed in a matrix along an X direction and a Y direction intersecting (in the embodiment, orthogonal to) the X direction. An ultrasonic array AL is formed of the plurality of ultrasonic transducers 45.

Configuration of Element Substrate

The element substrate 41 corresponds to a first substrate and includes a substrate main body 411 and a vibration film 412 laminated on the substrate main body 411. The element substrate 41 is provided with piezoelectric elements 413, lower electrode connection lines 414, wiring portions 415, an upper electrode extraction line 416, and bonding portions 417 on the vibration film 412 on the sealing plate 42 side. The ultrasonic transducer 45 which transmits and receives an ultrasonic wave is formed of a flexible film 412A and the piezoelectric element 413 in a vibration region of the vibration film 412 among the constituent elements. In plan view in which the element substrate 41 is viewed from a substrate thickness direction, a central region of the element substrate 41 is an array region Ar1 in which the ultrasonic array AL formed of a plurality of ultrasonic transducers 45 is provided. The array region Ar1 corresponds to a functional region. The plurality of ultrasonic transducers 45 are disposed in a matrix in the array region Ar1.

Here, in the following description, a surface of the element substrate 41 that is opposite to the sealing plate 42 will be referred to as a rear surface 41A corresponding to a first surface, and a surface on an opposite side to the rear surface 41A will be referred to as an operation surface 41B. A normal direction to the operation surface 41B is substantially the same as the Z direction, and a direction (first direction) from the element substrate 41 toward the sealing plate 42 is substantially parallel to the Z direction.

The substrate main body 411 is, for example, a semiconductor substrate made of Si or the like, for example. An opening 411A corresponding to each ultrasonic transducer 45 is provided in the array region Ar1 in the substrate main body 411. The respective openings 411A are separated by a wall portion 411B. Each opening 411A is closed by the vibration film 412 provided on the substrate main body 411 on the protective film 44 side (+Z side).

The vibration film 412 is formed of, for example, $SiO_2$, or a laminate of $SiO_2$ and $ZrO_2$, and is provided to cover the entire −Z side of the substrate main body 411. In the vibration film 412, a portion closing the opening 411A forms the flexible film 412A which is elastically deformed. A thickness dimension (thickness) of the vibration film 412 is a sufficiently small thickness dimension (thickness) relative to the substrate main body 411. In a case where the substrate main body 411 is made of Si, and the vibration film 412 is made of $SiO_2$, for example, the substrate main body 411 is subject to oxidation treatment, and thus the vibration film 412 having a desired thickness dimension (thickness) can be easily formed. In this case, the substrate main body 411 is etched with the vibration film 412 of $SiO_2$ as an etching stopper, and thus the opening 411A can be easily formed.

Each piezoelectric element 413 is provided on the flexible film 412A of the vibration film 412 closing the openings 411A. A single ultrasonic transducer 45 is formed of the flexible film 412A and the piezoelectric element 413. The piezoelectric element 413 is formed of a laminate of a lower electrode 413A, a piezoelectric film 413B, and an upper electrode 413C.

The lower electrode 413A or the upper electrode 413C is configured to include a layer made of one or two or more conductive materials. As such a conductive material, for example, electrode materials such as Au, Al, Cu, Ir, Pt, IrOx, Ti, TiW, and TiOx may be used. In the embodiment, for example, the lower electrode 413A is formed by laminating a TiW layer (50 nm) and a Cu layer (100 nm) in this order on the vibration film 412.

The piezoelectric film 413B is formed by using, for example, a transition metal oxide having a perovskite structure, more specifically, lead zirconate titanate containing Pb, Ti, and Zr.

A rectangular wave voltage with a predetermined frequency is applied between the lower electrode 413A and the upper electrode 413C in the ultrasonic transducer 45, and thus an ultrasonic wave can be transmitted by causing the flexible film 412A located in the opening region of the opening 411A to vibrate along the Z direction. If the flexible film 412A vibrates due to an ultrasonic wave reflected from a target object, a potential difference occurs in the upper and lower portions of the piezoelectric film 413B. Therefore, the received ultrasonic wave can be detected by detecting the potential difference occurring between the lower electrode 413A and the upper electrode 413C.

In the embodiment, as shown in FIG. 3, among the plurality of ultrasonic transducers 45 disposed along the X direction and the Y direction, two ultrasonic transducers 45 arranged in the Y direction form an ultrasonic transducer group 45A which is a single transmission/reception channel. In other words, the ultrasonic array AL has a two-dimensional array structure in which the ultrasonic transducer groups 45A are disposed at the substantially same interval along the X direction and the Y direction. That is, the ultrasonic array AL is a two-dimensional array formed by arranging a plurality of transmission/reception channels along the X direction and the Y direction.

Here, the lower electrodes 413A forming the ultrasonic transducer groups 45A are connected to each other via the lower electrode connection line 414. The lower electrode connection line 414 is integrally formed with the respective lower electrodes 413A and, thus, connects the lower electrodes 413A to each other. In other words, similar to the lower electrode 413A, the lower electrode connection line 414 is formed by laminating a TiW layer (50 nm) and a Cu layer (100 nm), and has a thickness dimension (thickness) of 150 nm, for example. The lower electrode connection line 414 may be provided separately from the lower electrode 413A.

The wiring portion 415 is provided on the lower electrode connection line 414 configured as mentioned above.

The wiring portion 415 which is conductive includes a main body part 415A and a coating part 415B coating the main body part 415A. As shown in FIG. 3, the wiring portion 415 is formed at a position overlapping the wall portion 411B in plan view viewed from the Z direction and has a substantially rectangular external shape. As shown in FIGS. 4 and 5, the wiring portion 415 protrudes from the lower electrode connection line 414 toward the sealing plate 42 side so as to be in contact with and electrically connected to the first conduction portion 421 provided on the sealing plate 42 side. In other words, the lower electrode 413A of each ultrasonic transducer 45 is electrically connected to the first conduction portion 421 on the sealing plate 42 side via the lower electrode connection line 414 and the wiring portion 415. A mounting structure is configured to include at least the element substrate 41, the wiring portion 415, the sealing plate 42, and the first conduction portion 421.

The main body part 415A is formed by using a conductive metal material. The main body part 415A protrudes toward the sealing plate 42 side from a position overlapping the wall portion 411B on the lower electrode connection line 414 in plan view viewed from the Z direction. The main body part 415A is formed by depositing Cu which is the metal material on the lower electrode connection line 414, for example, according to an electroplating method. The main body part 415A is formed to be, for example, 10 μm in both of a dimension (width dimension) in the Y direction and a dimension (height dimension) in the Z direction. A width dimension of the wall portion 411B is, for example, about 20 μm.

The coating part 415B is formed by using a conductive metal material and is formed to cover a surface of the main body part 415A. The coating part 415B is formed by laminating a Ni layer (50 nm) and an Au layer (100 nm) from the main body part 415A side. As mentioned above, the coating part 415B is formed by using a material such as Au having a relatively high electric conductivity, and thus it is possible to reduce contact resistance with the first conduction portion 421.

The coating part 415B is not limited to the configuration in which the Ni layer (50 nm) and the Au layer (100 nm) are laminated and may be formed by using various conductive materials.

As shown in FIG. 5, an end surface (hereinafter, also referred to as an end part 415C) of the wiring portion 415 on the sealing plate 42 side is located further toward the sealing plate 42 side than an end surface (hereinafter, also referred to as an end part 413D) on the −Z side of the piezoelectric element 413 of the ultrasonic transducer 45. In the embodiment, the end part 415C is located further toward the sealing plate 42 side than a −Z side end part Rz of a vibration range of the ultrasonic transducer 45.

In the wiring portion 415, a ratio of a dimension (height dimension) in the Z direction to a minimum dimension (a width dimension which is a dimension in the Y direction in the embodiment) in an XY section of the wiring portion 415, that is, an aspect ratio, is preferably 0.1 or more and 5 or less and is more preferably 0.1 or more and 1 or less. Consequently, it is possible to prevent the wiring portion 415 from being deformed or inclined by pressure from the first conduction portion 421, and thus to improve the reliability of electrical connection.

A planar shape of the wiring portion 415 in plan view viewed from the Z direction is not limited to a rectangular shape and may be a circular shape, an elliptical shape, various polygonal shapes, or the like.

Each upper electrode 413C of the ultrasonic transducer 45 is electrically connected to the upper electrode extraction line 416 and is electrically connected to the second conduction portion 424 on the sealing plate 42 side in a wiring region Ar2 outside the array region Ar1.

The upper electrode extraction line 416 which corresponds to an extraction wire and is made of a conductive material is integrally formed with, for example, the upper electrode 413C and includes a plurality of extraction portions 416A disposed along the Y direction, connection portions 416B connecting the extraction portions 416A and the upper electrodes 413C to each other, and electrical connection portions 416C disposed in the wiring region Ar2.

For example, as shown in FIG. 3, each of the extraction portions 416A is disposed between the odd-numbered and even-numbered ultrasonic transducer groups 45A, for example, when counted along the X direction, and the upper electrodes 413C of the ultrasonic transducer groups 45A are connected to each other via the connection portion 416B.

The electrical connection portions 416C are formed outside of the array region Ar1 such as in the wiring regions Ar2 in outer peripheral portions of the element substrate 41 on the ±Y sides and are connected to the extraction portions 416A. In FIG. 3, only the electrical connection portion 416C on the +Y side is shown. The electrical connection portion 416C is in contact with and is electrically connected to the second conduction portion 424 (refer to FIG. 4) provided on the sealing plate 42 side. In other words, the upper electrode 413C is electrically connected to the second conduction portion 424 on the sealing plate 42 side via the upper electrode extraction line 416. Each upper electrode 413C is connected to a ground circuit (not shown) of the circuit substrate 23 via a wiring formed on the sealing plate 42 and is set as a reference potential.

Since the electrical connection portion 416C is formed in the wiring region Ar2 in the outer peripheral portion of the element substrate 41, the electrical connection portion can be more increased in a width dimension (dimension in the Y direction) than the electrical connection portion that is formed in the array region Ar1. In the embodiment, the electrical connection portion 416C has a larger width dimension than a dimension (width dimension) of the wiring portion 415 in the Y direction large, which is connected to the first conduction portion 421. Thus, it is possible to increase a contact area with the second conduction portion 424, and thus it is possible to reduce contact resistance with the second conduction portion 424. The electrical connection portion 416C is formed by using a conductive material such as Au having a relatively high electric conductivity, and thus it is possible to more reduce the contact resistance.

The bonding portion 417 bonds the element substrate 41 configured as described above to the sealing plate 42. The bonding portion 417 includes a first bonding part 417A that is disposed along the outer edge of the element substrate 41 and a second bonding part 417B that is disposed along the ultrasonic transducer 45.

The bonding portion 417 is formed by using a material which can bond the element substrate 41 to the sealing plate 42, for example, various adhesives or a resin material such as a photosensitive resin material (photoresist). In the embodiment, the bonding portion 417 is formed by using a photosensitive resin material. Consequently, the bonding portion 417 can be formed at a desired position in a desired shape.

As shown in FIG. 3 as an example, the second bonding parts 417B are disposed along the X direction at the positions overlapping the wall portions 411B on the surface of the vibration film 412 on the sealing plate 42 side. The first bonding part 417A and the second bonding part 417B are formed on the vibration film 412, that is, in the region in which the upper electrode extraction line 416 and the like are not formed. Consequently, thickness dimensions (thicknesses) the first bonding part 417A and the second bonding part 417B can be made uniform regardless of a formation position.

The second bonding part 417B is disposed between the extraction portions 416A of the upper electrode extraction line 416, that is, the second bonding parts are disposed at positions with each wiring portion 415 interposed therebetween in the Y direction. In this configuration, the second bonding parts 417B can be disposed such that distances between the respective wiring portions 415 and the second bonding parts 417B are the same as each other. Therefore, the stress from the second bonding parts 417B can be substantially uniformly applied to the respective connection positions of the wiring portions 415.

The second bonding parts 417B may be formed along the X direction. The second bonding parts 417B are not limited to the configuration of being directly provided on the vibration film 412 and may be disposed on the extraction portion 416A of the upper electrode extraction line 416 along the X direction.

Further, the second bonding parts 417B may be disposed with each of the wiring portions 415 interposed therebetween in the Y direction, for example, may be disposed on the +Y side of the wiring portions 415. The second bonding part 417B is formed in at least the array region Ar1, and thus the connection reliability between the wiring portion 415 and the first conduction portion 421 can be improved compared with a case where only the first bonding part 417A is provided.

Configuration of Sealing Plate

The sealing plate 42 shown in FIGS. 4 to 6 corresponds to a second substrate, is provided for reinforcing the strength of the element substrate 41, for example, is configured of a semiconductor substrate or the like, and is bonded to the element substrate 41 with the bonding portion 417. A material or a thickness of the sealing plate 42 influences frequency characteristics of the ultrasonic transducer 45, and is thus preferably set on the basis of a center frequency of a transmitted and received ultrasonic wave.

The sealing plate 42 is provided with the first conduction portion 421 corresponding to the conduction portion, a first through-electrode 422, a lower electrode wire 423, the second conduction portion 424 corresponding to the second conduction portion, a second through-electrode 425, and an upper electrode wire 426.

Configuration of First Conduction Portion

The first conduction portion 421 shown in FIGS. 4 to 6 corresponds to the connection portion, is provided on a surface (corresponding to a second surface, hereinafter, also referred to as an inner surface 42A) of the sealing plate 42 on the element substrate 41 side, is in pressure and close contact with the wiring portion 415 provided on the element substrate 41, and is electrically connected to the wiring portion 415. The first conduction portion 421 includes a first resin part 421A and a first conductive film 421B that covers the first resin part 421A and is electrically connected to the first through-electrode 422.

The first resin part 421A corresponds to a resin part, is provided on the inner surface 42A at a position overlapping each of the wiring portions 415 as shown in FIG. 5, and protrudes from the inner surface 42A toward the element substrate 41. The first resin part 421A is made of an elastic resin material and is formed in a substantially hemispherical shape by thermally melting a resin material disposed on the inner surface 42A as will be described below. The first resin part 421A may be formed in a substantially trapezoidal shape (a state in which corners of a trapezoid are rounded) according to the kind of resin material, or a temperature condition in thermal melting.

A photosensitive resin material (photoresist) is used as a material of which the first resin part 421A is formed. In this case, the first resin part 421A may be formed in a desired shape at a desired position. As a material of which the first resin part 421A is formed, not only a photosensitive resin material, but also various elastic resin materials, for example, polyimide resin, acrylic resin, phenol resin, epoxy resin, silicone resin, and modified polyimide resin may be used.

The first conductive film 421B corresponds to the conductive part, is made of a conductive material, and coats the first resin part 421A. The first conductive film 421B extends to a formation position of the first through-electrode 422 along the Y direction and is connected to the first through-electrode 422. A thickness of the first conductive film 421B is made sufficiently smaller than a thickness of the first resin part 421A, and thus the first conductive film 421B can be deformed according to elastic deformation of the first resin part 421A.

As a conductive material of which the first conductive film 421B is formed, Au, Ag, TiW, Cu, Ni, Pd, Al, Cr, Ti, W, NiCr, a lead-free solder, or the like may be used. In the embodiment, for example, the first conductive film 421B is formed by laminating a TiW layer (50 nm) and an Au layer (100 nm) in this order from the inner surface 42A side. In this configuration, the Au layers located on the respective surfaces of the first conductive film 421B and the coating part 415B of the wiring portion 415 can be bonded to each other through diffusion bonding. Consequently, the reliability of electrical connection between the first conduction portion 421 and the wiring portion 415 can be further improved.

As shown in FIGS. 4 and 5, the first conduction portion 421 configured as mentioned above is in pressure contact with the end part 415C of the wiring portion 415, and thus the first resin part 421A and the first conductive film 421B are elastically deformed. In this case, the +Z side end part of the first conduction portion 421 is deformed along the end part 415C and is thus in close contact with the end part 415C in a first connection region C1 (refer to FIG. 6). As mentioned above, since the first resin part 421A and the first conductive film 421B are elastic, the first conduction portion 421 and the end part 415C can be made in close contact with each other, and thus it is possible to improve the reliability of electrical connection between the first conduction portion 421 and the wiring portion 415.

Here, as shown in FIG. 5, a connection position between the first conduction portion 421 and the wiring portion 415 is located further toward the sealing plate 42 side than the end part 413D of the piezoelectric element 413, similar to the end part 415C of the wiring portion 415. In other words, in this configuration, the shortest distance (a distance of a location where a distance between the end part 413D of the piezoelectric element 413 and the sealing plate 42 is shortest) between the end part 413D of the piezoelectric element 413 and the sealing plate 42 is longer than the longest distance (a distance of a location where a distance between the connection position and the sealing plate 42 is longest) between the sealing plate 42 and the connection position where the first conduction portion 421 and the wiring portion 415 are connected to each other. Further in other words, in this configuration, the shortest distance between the end part 413D of the piezoelectric element 413 and the inner surface 42A of the sealing plate 42 is longer than the longest distance between the connection position where the first conduction portion 421 is connected to the wiring portion 415 and the inner surface 42A of the sealing plate 42. In the embodiment, the connection position is located further toward the sealing plate 42 side than the −Z side end part Rz of the vibration range of the ultrasonic transducer 45. Consequently, it is possible to suppress interference between the ultrasonic transducer 45 and the first conduction portion 421. The first conduction portion 421 is in contact with the end part 415C of the wiring portion 415, and thus wiring connection between the element substrate 41 and the sealing plate 42 can be performed. Therefore, as described above, the connection position is located further toward the sealing plate 42 side than the piezoelectric element 413, and thus wiring connection can be easily performed. Since a connection position can be set according to a dimension of the wiring portion 415, it is possible to easily adjust a connection position according to the piezoelectric element 413.

The first conduction portion 421 has a curved part 421C which is curved toward the sealing plate 42 from the first connection region C1 (in a case where the end part 415C of the wiring portion 415 is flat, the connection position where the first conduction portion 421 is connected to the wiring portion 415 is the first connection region C1 in plan view) to the outside in the surface direction (a surface direction of the XY plane) of the rear surface 41A. That is, the curved part 421C is curved to be separated from the piezoelectric element 413 toward the piezoelectric element 413 side along the XY plane. In other words, an area of the region in which the first conduction portion 421 is bonded to the sealing plate 42 is larger than an area of the region (first connection region C1) in which the wiring portion 415 is connected to the first conduction portion 421. Further in other words, of perpendicular lines that can be drawn from a region occupied when the piezoelectric element 413 is projected in the first direction to the first conduction portion 421, a perpendicular line that can be drawn to a position at which the first conduction portion 421 is bonded to the sealing plate 42 is shorter than a perpendicular line that can be drawn to a position at which the wiring portion 415 is connected to the first conduction portion 421. Consequently, it is possible to suppress interference between the ultrasonic transducer 45 and the first conduction portion 421.

Further, the first resin part 421A is substantially hemispherical during formation, and the end surface (surface of the first resin part 421A that comes into contact with the sealing plate 42) on the inner surface 42A is substantially circular. In a case where a diameter (that is, the maximum dimension or the maximum diameter) of the end surface is indicated by $L_1$, a distance d1 from the sealing plate 42 to the −Z side end part Rz of the vibration range of the ultrasonic transducer 45 satisfies the following Expression (1). Consequently, it is possible to further suppress interference between the ultrasonic transducer 45 and the first conduction portion 421. In other words, in a case where the first conduction portion 421 is not elastically deformed, a tip end thereof on the +Z side is located at a distance of about $L_1/2$ from the sealing plate 42. Therefore, since the distance d1 satisfies the following Expression (1), the first conduction portion 421 can be disposed outside the drive range of the ultrasonic transducer 45.

Since the first conduction portion 421 is elastically deformed in practice, a distance from the sealing plate 42 to the tip end on the +Z side is smaller than $L_1/2$. Therefore, a distance d2 between the end part 413D of the piezoelectric element 413 and the sealing plate 42 during drive stoppage satisfies the following Expression (2), and thus it is also possible to suppress interference between the ultrasonic transducer 45 and the first conduction portion 421.

Expression 1: $d1 > L_1/2$ (1)

$d2 > L_1/2$ (2)

Configurations of First Through-electrode and Lower Electrode Wire

As shown in FIGS. 4 to 6, a pair of first through-electrodes 422 are provided at positions with the first resin part 421A interposed therebetween along the Y direction and may be, for example, a Si through-electrode (through-silicon via: TSV) or may employ a configuration in which a through-hole is filled with a conductive material. The lower electrode wire 423 is individually formed with respect to each first through-electrode 422 on the −Z side surface (hereinafter, referred to as an outer surface 42B) of the sealing plate 42. The lower electrode wire 423 is connected to the first through-electrode 422 and is connected to the circuit substrate 23 via a wiring (not shown) formed along the outer surface 42B.

At least one first through-electrode 422 may be formed, and three or more through-electrodes may be formed. A position where the first through-electrode 422 is formed is not limited to the above-described position, and the first through-electrode may be formed on, for example, the +X side or −X side of the first resin part 421A in plan view viewed from the Z direction.

Configuration of Second Conduction Portion

The second conduction portion 424 shown in FIGS. 4 and 6 corresponds to a second conduction portion, is provided on the inner surface 42A of the sealing plate 42, is in pressure and close contact with the electrical connection portion 416C of the upper electrode extraction line 416 provided on the element substrate 41, and is electrically connected to the electrical connection portion 416C. The second conduction portion 424 includes a second resin part 424A and a second conductive film 424B and is configured in the substantially same manner as the first conduction portion 421 although having a larger size than that of the first conduction portion 421. A dimension (height dimension) of the second conduction portion 424 in the Z direction in a case without elastic deformation is substantially equal to a sum of a dimension (height) of the first conduction portion 421 and a dimension (height) of the wiring portion 415.

The second resin part 424A corresponds to a second resin part, and a plurality of second resin parts are provided on the inner surface 42A at a positions overlapping the electrical connection portion 416C as shown in FIG. 6 and protrude from the inner surface 42A toward the element substrate 41. Similar to the first resin part 421A, the second resin part 424A is formed by using an elastic resin material.

Here, similar to the first resin part 421A, the second resin part 424A is formed in a substantially hemispherical shape (the second resin part 424A may be formed in a substantially trapezoidal shape according to the kind of resin material or a temperature condition in thermal melting), and an end surface (a surface of the second resin part 424A that comes into contact with the sealing plate 42) on the inner surface 42A side is substantially circular. A diameter (that is, the maximum dimension or the maximum diameter) $L_2$ (refer to FIG. 4) is set to be larger than the diameter $L_1$ of the first resin part 421A (refer to FIG. 5). At least one second resin part 424A may be formed at a position of overlapping the electrical connection portion 416C.

Similar to the first conductive film 421B, the second conductive film 424B corresponds to a second conductive part, is made of a conductive material, and coats the second resin part 424A. The second conductive film 424B extends to a formation position of the second through-electrode 425 and is connected to the second through-electrode. A thickness of the second conductive film 424B is made sufficiently smaller than a thickness of the second resin part 424A, and thus the second conductive film 424B can be deformed according to elastic deformation of the second resin part 424A. In a case where the surface of the electrical connection portion 416C and the surface of the second conductive film 424B are formed of the Au layers, the second conduction portion 424 can be bonded to the electrical connection portion 416C through diffusion bonding between the Au layers.

As illustrated in FIG. 4, the second conduction portion 424 configured as mentioned above is in pressure contact with the electrical connection portion 416C and thus is elastically deformed. In this case, the +Z side end part of the second conduction portion 424 is deformed along the electrical connection portion 416C and is thus in close contact with the electrical connection portion 416C in a second connection region C2 (refer to FIG. 6). As mentioned above, since the first resin part 421A and the first conductive film 421B are elastic, the first conduction portion 421 and the end part 415C can be made in close contact with each other, and thus it is possible to improve the reliability of electrical connection between the second conduction portion 424 and the electrical connection portion 416C.

Configurations of Second Through-Electrode and Upper Electrode Wire

As shown in FIGS. 4 and 6, the second through-electrode 425 is disposed in the vicinity of the second resin part 424A. The upper electrode wire 426 is individually formed with respect to each second through-electrode 425 on the outer surface 42B of the sealing plate 42. The upper electrode wire 426 is connected to the second through-electrode 425 and is connected to the circuit substrate 23 via a wiring (not shown) formed along the outer surface 42B.

Configurations of Acoustic Matching Layer and Protective Film

The acoustic matching layer 43 is disposed on the element substrate 41 on the operation surface 41B side. In the embodiment, the acoustic matching layer 43 fills the opening 411A formed on the operation surface 41B side.

The protective film 44 is provided on the element substrate 41 and the acoustic matching layer 43, so as to protect the element substrate 41 and the acoustic matching layer 43. As shown in FIG. 1, the protective film 44 is exposed to the outside from the sensor window 21B of the case 21 and is brought into contact with a living body surface during ultrasonic measurement.

The acoustic matching layer 43 or the protective film 44 causes an ultrasonic wave transmitted from the ultrasonic transducer 45 to propagate through a living body, which is a measurement target, with high efficiency and causes an ultrasonic wave reflected inside the living body to propagate to the ultrasonic transducer 45 with high efficiency. Thus, acoustic impedance of the acoustic matching layer 43 and the protective film 44 is set to a value similar to acoustic impedance of the living body.

Configuration of Circuit Substrate

The circuit substrate 23 is provided with a driver circuit or the like which is bonded to the ultrasonic device so as to control the ultrasonic transducer 45. As illustrated in FIG. 2, the circuit substrate 23 includes a selection circuit 231, a transmitting circuit 232, and a receiving circuit 233.

In the embodiment, a wiring connected to the upper electrode 413C which is a common electrode of the ultrasonic transducers 45 is connected to a ground circuit or the like in the circuit substrate 23, for example. Consequently, the upper electrode 413C is set to a predetermined common potential (for example, 0 potential).

The selection circuit 231 is connected to the lower electrode wire 423 extracted from each ultrasonic transducer group 45A. The selection circuit 231 switches between connection states transmitting connection for connecting the ultrasonic sensor 24 to the transmitting circuit 232 and receiving connection for connecting the ultrasonic sensor 24 to the receiving circuit 233 under the control of the control device 10.

When the connection is switched to the transmitting connection in accordance with the control of the control device 10, the transmitting circuit 232 outputs a transmitting signal indicating that the ultrasonic wave is transmitted to the ultrasonic sensor 24 via the selection circuit 231.

When the connection is switched to the receiving connection in accordance with the control of the control device 10, the receiving circuit 233 outputs a received signal input from the ultrasonic sensor 24 via the selection circuit 231, to the control device 10. The receiving circuit 233 is configured to include, for example, a low-noise amplification circuit, a voltage controlled alternator, a programmable gain amplifier, a low-pass filter, and an A/D converter, performs various signal processes such as conversion of the received signal into a digital signal, removal of a noise component, and amplification to a desired signal level, and then outputs the processed received signal to the control device 10.

Configuration of Control Device

As shown in FIG. 2, the control device 10 corresponds to a controller and is configured to include, for example, an operation unit 11, a display unit 12, a storage unit 13, and a calculation unit 14. The control device 10 may employ, for example, a terminal device such as a tablet terminal, a smartphone, or a personal computer and may be a dedicated terminal device for operating the ultrasonic probe 2.

The operating unit 11 is a user interface (UI) through which a user operates the ultrasonic measuring apparatus 1 and may be formed of, for example, a touch panel provided on the display unit 12, operation buttons, a keyboard, and a mouse.

The display unit 12 is formed of, for example, a liquid crystal display and displays an image.

The storage unit 13 stores various programs or various pieces of data for controlling the ultrasonic measuring apparatus 1.

For example, the calculation unit 14 is configured to have an arithmetic circuit such as a central processing unit (CPU), and the storage circuit such as a memory. The calculation unit 14 reads various programs stored in the storage unit 13 and executes the programs so as to control processes for causing the transmitting circuit 232 to generate and output a transmission signal, and to perform control for setting of a frequency of a received signal or gain setting in the receiving circuit 233.

Manufacturing Method of Ultrasonic Device

Hereinafter, a description will be made of a manufacturing method of the above-described ultrasonic device 22.

Figure 7:
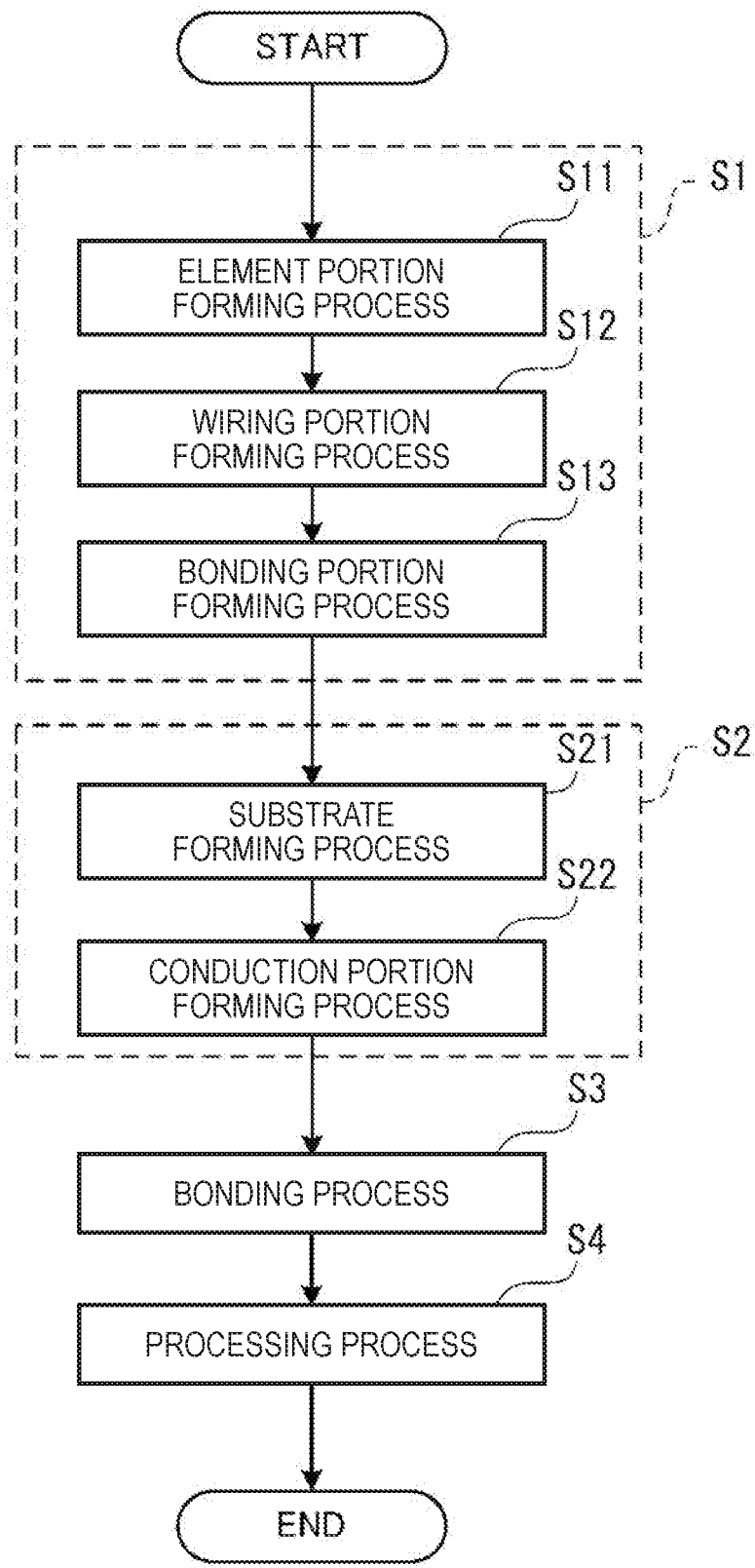
FIG. 7 is a flowchart showing an example of a manufacturing method of the ultrasonic device according to the first embodiment.

FIG. 7 is a flowchart showing an example of a manufacturing method of the ultrasonic device 22. FIGS. 8 to 12C illustrate views schematically showing manufacturing processes of the ultrasonic device 22.

In order to manufacture the ultrasonic device 22, as shown in FIG. 7, an element substrate forming process S1, a sealing plate forming process S2, a bonding process S3, and a processing process S4 are executed.

FIGS. 8 to 12C schematically show sections in the vicinity of the ultrasonic transducer group 45A shown in FIG. 4.

Element Substrate Forming Process

Figure 8:
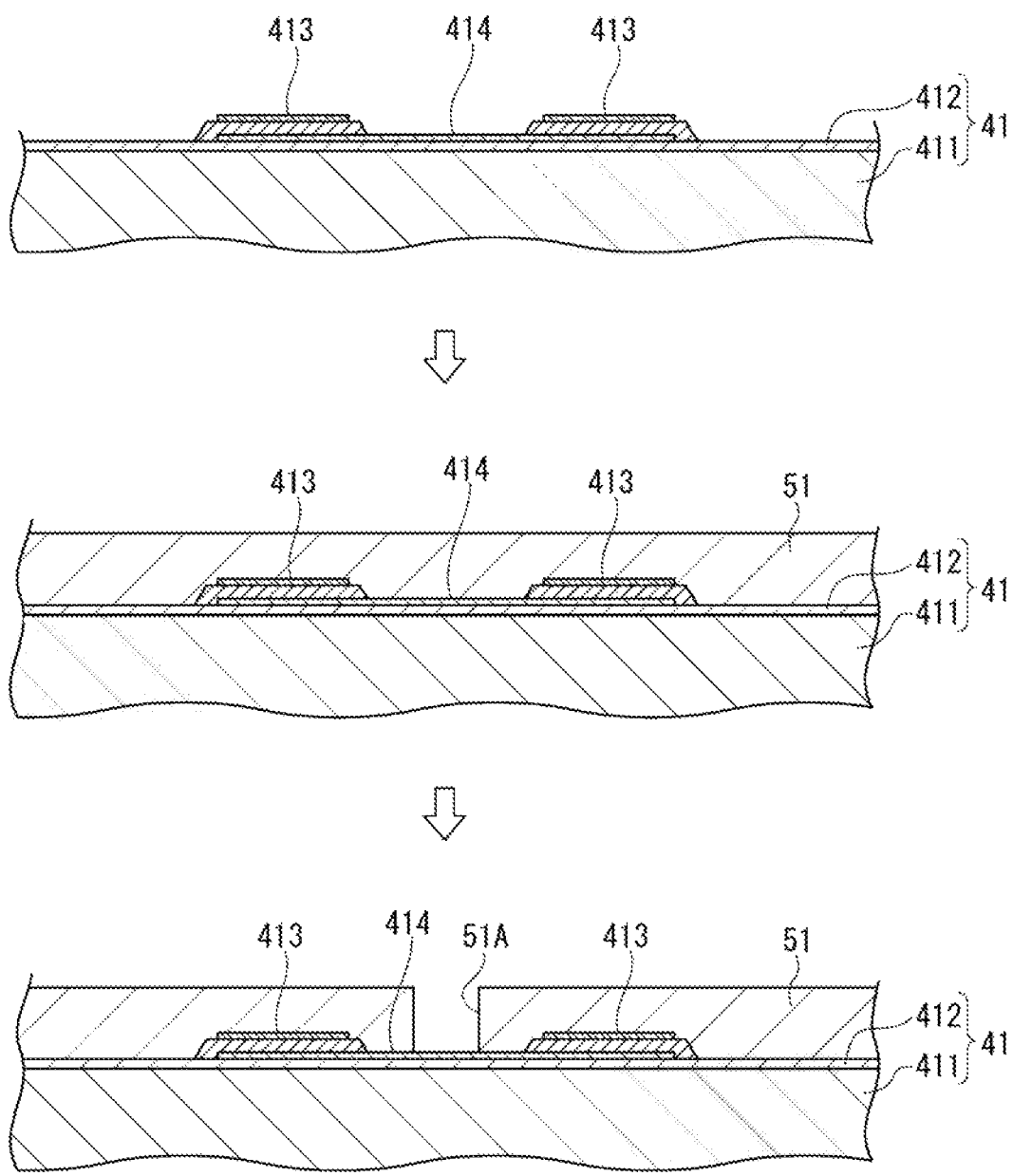
FIG. 8 illustrates sectional views schematically showing an example of a manufacturing process of the ultrasonic device according to the first embodiment.
Figure 9:
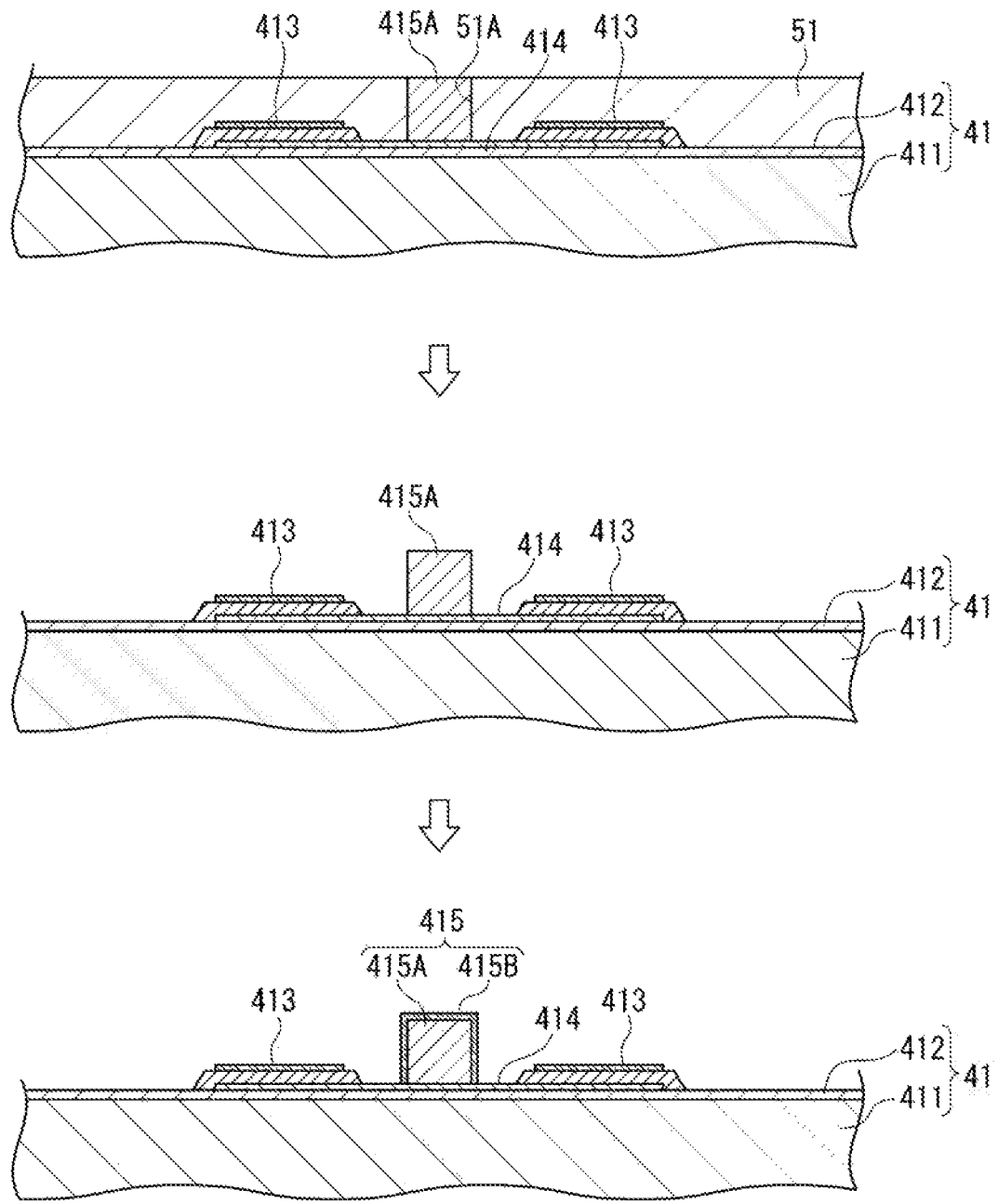
FIG. 9 illustrates sectional views schematically showing an example of a manufacturing process of the ultrasonic device according to the first embodiment.
Figure 10:
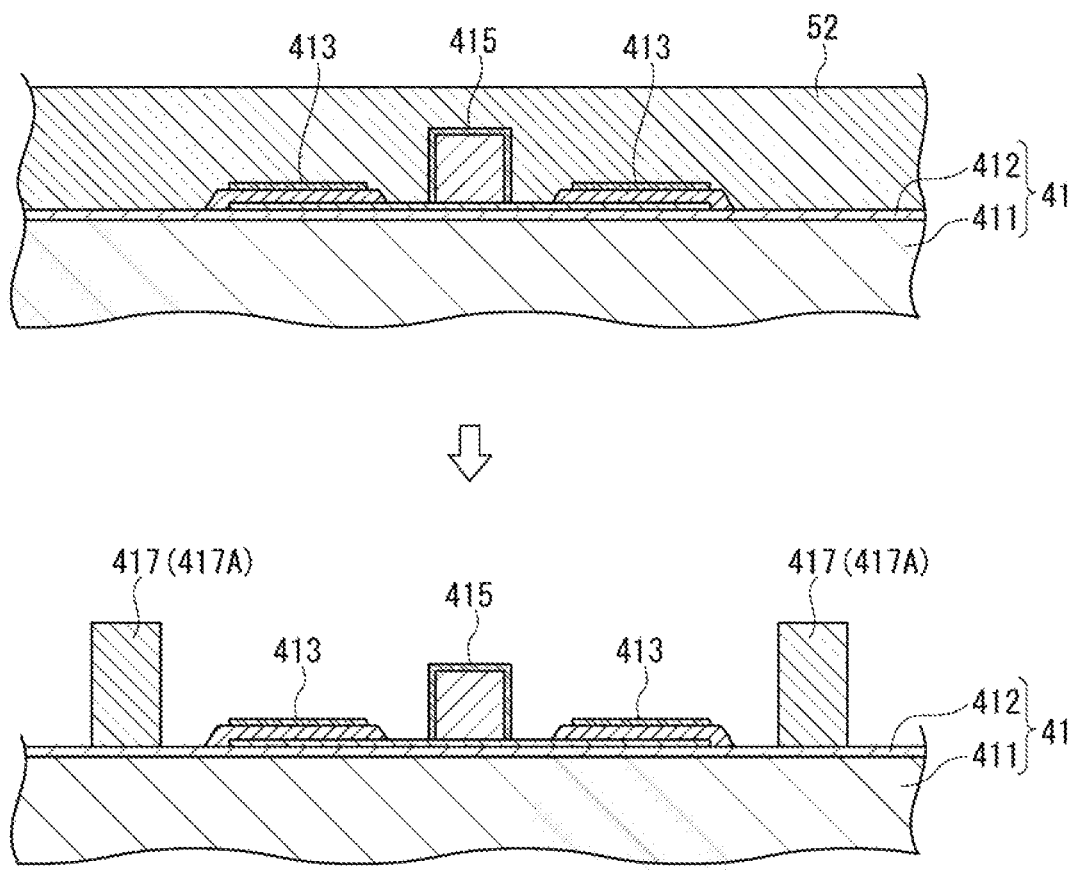
FIG. 10 illustrates sectional views schematically showing an example of a manufacturing process of the ultrasonic device according to the first embodiment.

As shown in the top row of FIG. 8, in the element substrate forming process S1, first, for example, the vibration film 412, the piezoelectric elements 413, the lower electrode connection line 414, and the upper electrode extraction line 416 (not shown) are formed on the substrate main body 411 made of Si (Step S11: element portion forming process). In Step S11, a film of Zr is formed on a film of $SiO_2$ which is formed by performing thermal oxidation treatment on the substrate main body 411, and thermal oxidation treatment is further performed so as to form a layer of $ZrO_2$ and thus to form the vibration film 412. The lower electrode 413A, the piezoelectric film 413B, and the upper electrode 413C are formed on the vibration film 412, and thus the piezoelectric element 413 is formed. The lower electrode connection line 414 is formed when the lower electrode 413A is formed, and the upper electrode extraction line 416 is formed when the upper electrode 413C is formed. Specifically, first, an electrode material formed as a film on the vibration film 412 through, for example, sputtering is patterned, and thus the lower electrode 413A and the lower electrode connection line 414 are formed. Thereafter, the piezoelectric film 413B is formed on the lower electrode 413A. After the piezoelectric film 413B is formed, similar to the lower electrode 413A and the lower electrode connection line 414, the upper electrode 413C and the upper electrode extraction line 416 are formed.

Next, as shown in FIG. 7, the wiring portion 415 is formed on the lower electrode connection line 414 (Step S12: wiring portion forming process). In Step S12, as shown in the middle row of FIG. 8, a photosensitive resin layer 51 is formed. In this case, a thickness of the photosensitive resin layer 51 is adjusted such that a thickness dimension (thickness) of the photosensitive resin layer 51 on the lower electrode connection line 414 is equal to a thickness dimension (thickness) of the main body part 415A of the wiring portion 415. In the embodiment, the photosensitive resin layer 51 is formed to have a thickness of, for example, 10 μm by using a positive photoresist. The photosensitive resin layer 51 is exposed and developed, as shown in the bottom row of FIG. 8, the photosensitive resin layer 51 at the formation position of the main body part 415A is removed, and a mask pattern having an opening 51A at the formation position is formed. As shown in the top row of FIG. 9, the main body part 415A is formed by depositing Cu on the lower electrode connection line 414 in the opening 51A according to an electroplating method, for example, and, as shown in the middle row of FIG. 9, the photosensitive resin layer 51 is removed. Thereafter, as shown in the bottom row of FIG. 9, the coating part 415B is formed on a surface of the main body part 415A according to an electroless plating method, for example. In the embodiment, a Ni layer having a thickness dimension (thickness) of 50 nm and an Au layer having a thickness dimension (thickness) of 100 nm are laminated in this order.

Next, as shown in FIG. 7, the bonding portions 417 are formed on the element substrate 41 (Step S13: bonding portion forming process). In Step S13, as shown in the top row of FIG. 10, for example, a photosensitive resin layer 52 for forming the bonding portions 417 is formed on the element substrate 41. In this case, a thickness of the photosensitive resin layer 52 is adjusted such that a thickness dimension (thickness) of the photosensitive resin layer 52 is equal to a thickness dimension (thickness) of the bonding portion 417 at a formation position of the bonding portion 417. In the embodiment, the bonding portion 417 is formed on the vibration film 412 at the respective formation positions, and thus thickness dimensions (thicknesses) are the same as each other. Thus, a surface of the photosensitive resin layer 52 may be formed to be flat, and a thickness is easily adjusted. The photosensitive resin layer 52 is formed to have a thickness of 22 μm and a width (the width in the Y direction shown in FIG. 4) of 10 μm at the formation position by using, for example, a negative photoresist. The photosensitive resin layer 52 is exposed and developed such that the bonding portions 417 are formed as shown in the bottom row of FIG. 10.

Sealing Plate Forming Process

Next, as shown in FIG. 7, the sealing plate forming process S2 is performed. In Step S2, as shown in the first row of FIG. 11, first, the sealing plate 42 provided with the first through-electrodes 422 and the second through-electrode 425 (not shown) is formed (Step S21: substrate forming process (refer to FIG. 7)).

Figure 11:
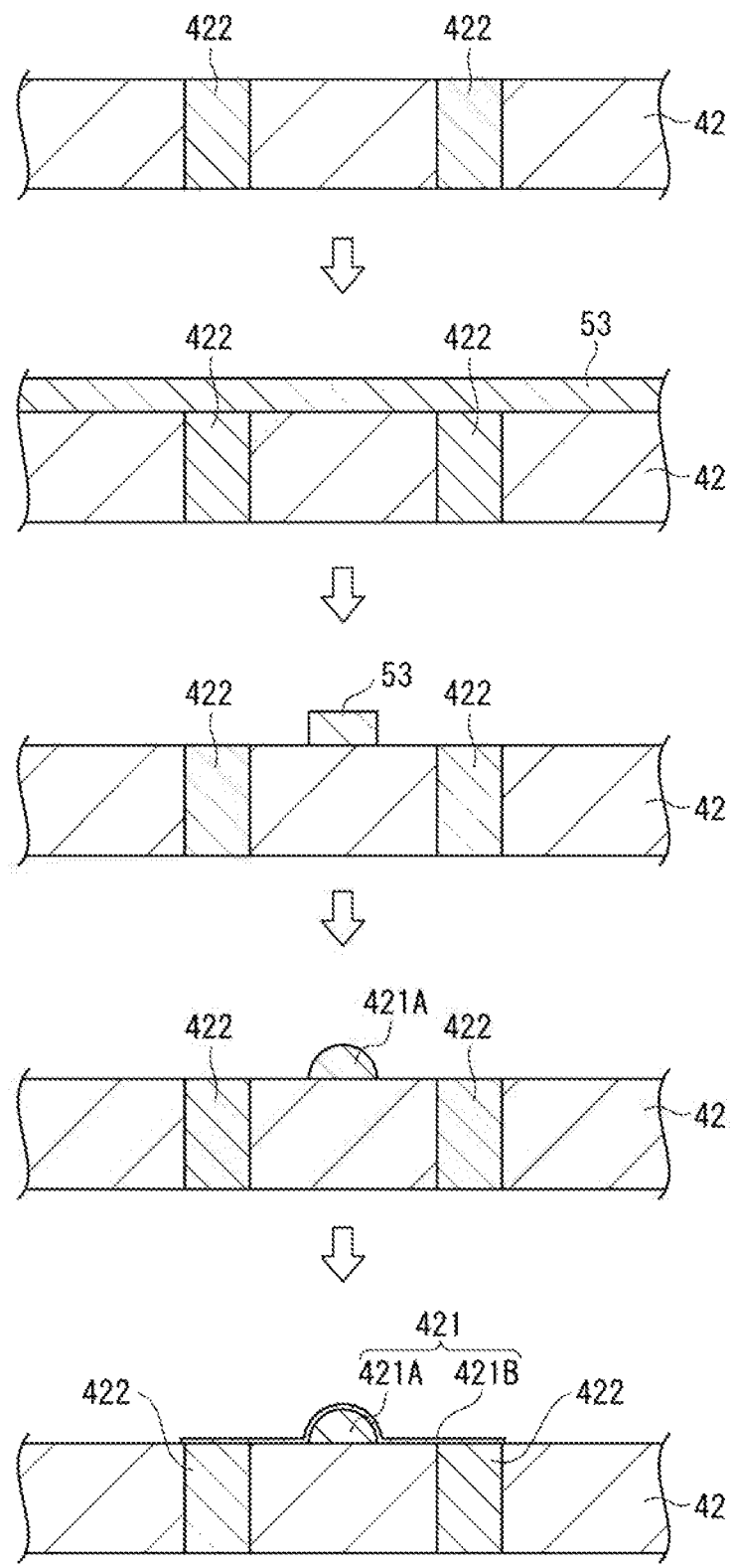
FIG. 11 illustrates sectional views schematically showing an example of a manufacturing process of the ultrasonic device according to the first embodiment.

Next, as shown in the second and subsequent rows of FIG. 11, the first conduction portion 421 and the second conduction portion 424 (not shown) are formed on the inner surface 42A side of the sealing plate 42 (Step S22: conduction portion forming process (refer to FIG. 7)). In Step S22, first, a resin layer 53 for forming the first resin part 421A is formed on the inner surface 42A of the sealing plate 42. Thereafter, the resin layer 53 formed at positions other than the formation position of the first resin part 421A is removed through etching. Next, the resin layer 53 is heated and melted, and is then solidified, and thus the substantially hemispherical first resin part 421A is formed. In the embodiment, the first resin part 421A is formed to have, for example, a width dimension (that is, the diameter $L_1$ of the surface on the inner surface 42A side) of 24 μm and a height dimension (height) of 12 μm. A shape of the first resin part 421A may be adjusted by using a volume of the resin layer 53 before being melted, the wettability of the inner surface 42A, or the like. For example, a TiW layer (50 nm) and an Au layer (100 nm) are laminated in this order as the first conductive film 421B. In Step S22, the second conduction portion 424 and the first conduction portion 421 are simultaneously formed. The second conduction portion 424 is formed to have larger width and height than that of the first conduction portion 421. For example, the second resin part 424A is formed to have a width dimension (width) of 44 μm and a height dimension (height) of 22 μm.

Bonding Process

Figure 12:
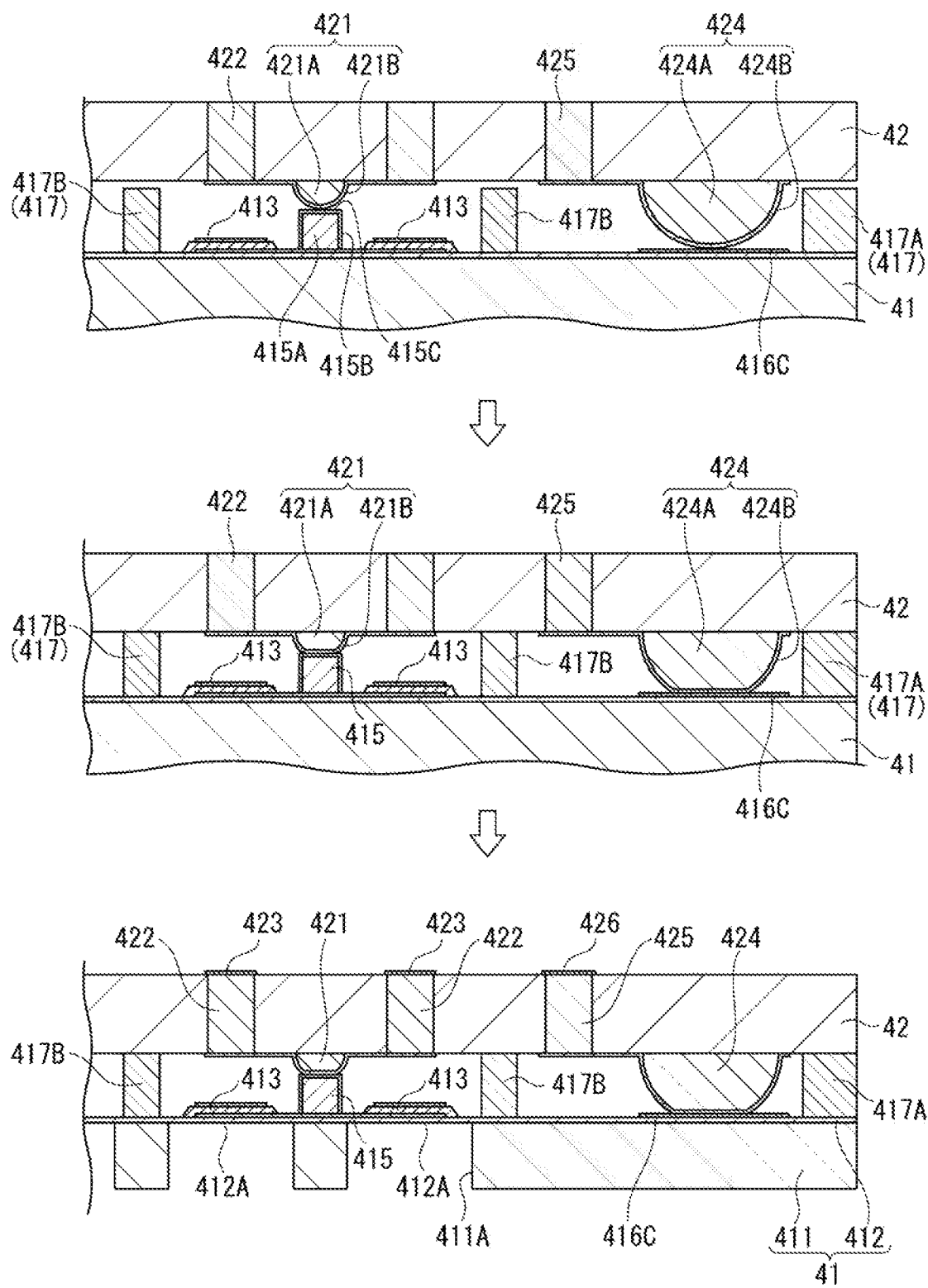
FIG. 12 illustrates sectional views schematically showing an example of a manufacturing process of the ultrasonic device according to the first embodiment.

Next, as shown in FIG. 7, a bonding process of bonding the element substrate 41 and the sealing plate 42 formed as described above together is performed (Step S3). In Step S3, as shown in FIG. 12, the sealing plate 42 is disposed on the element substrate 41. In this case, relative positions between the element substrate 41 and the sealing plate 42 are adjusted. In other words, positioning is performed so that the first conduction portion 421 overlaps the corresponding wiring portion 415, and the second conduction portion 424 overlaps the electrical connection portion 416C. As shown in the top row of FIG. 12, the height dimension (dimension in the Z direction) of the second conduction portion 424 is substantially equal to a sum of the height dimensions (heights) of the first conduction portion 421 and the wiring portion 415.

After the positioning is performed, at least one of the element substrate 41 and the sealing plate 42 is pressed in a direction in which the element substrate 41 and the sealing plate 42 come close to each other. Consequently, the first conduction portion 421 is elastically deformed so as to come into close contact with the wiring portion 415. Similarly, the second conduction portion 424 comes into close contact with the electrical connection portion 416C. In this state, the element substrate 41 and the sealing plate 42 are heated (for example, for an hour at 200° C.). Consequently, the bonding portion 417 is melted and is, then, solidified again, and thus the element substrate 41 and the sealing plate 42 are bonded to each other.

Processing Process

Next, as shown in FIG. 7, a processing process of processing the element substrate 41 and the sealing plate 42 is performed (Step S4). In Step S4, as shown in FIG. 12, a thickness of the substrate main body 411 of the element substrate 41 is adjusted, and then the openings 411A are formed. A wiring including the lower electrode wires 423 and the upper electrode wires 426 is formed on the outer surface 42B of the sealing plate 42. The wiring on the outer surface 42B side of the sealing plate 42 may be formed in advance. Thereafter, as shown in FIG. 4, the openings 411A are filled with the acoustic matching layer 43, and then the protective film 44 is formed. In the above-described way, the ultrasonic device 22 is manufactured.

Advantageous Effects of First Embodiment

In the embodiment, the end part 415C of the wiring portion 415 is located further toward the sealing plate 42 side than the end part 413D of the piezoelectric element 413. In other words, the connection position between the first conduction portion 421 and the wiring portion 415 is located further toward the sealing plate 42 side than the end part 413D of the piezoelectric element 413. In the embodiment, the connection position is located further toward the sealing plate 42 side than the −Z side end part Rz of the vibration range of the ultrasonic transducer 45. In this configuration, even if a position difference occurs in the first conduction portion 421, since a position of the first conduction portion 421 is located further toward the sealing plate 42 side than the piezoelectric element 413, it is possible to suppress interference between the ultrasonic transducer 45 and the first conduction portion 421.

Since interference between the ultrasonic transducer 45 and the first conduction portion 421 due to a position difference can be suppressed, it is possible to appropriately perform wiring connection between the element substrate 41 and the sealing plate 42 even if alignment accuracy is lower than in a case where the wiring portion 415 is not formed.

It is possible to adjust a connection position between the wiring portion 415 and the first conduction portion 421 according to a height dimension (height) of the wiring portion 415. Therefore, it is possible to easily adjust a connection position according to characteristics or the like of the ultrasonic transducer 45.

An aspect ratio of the wiring portion 415 is preferably 0.1 or more and 5 or less, and is about 1 in the embodiment. Here, if the aspect ratio is equal to or less than 5, it is possible to prevent the wiring portion 415 from being inclined or bent due to pressing force from the first conduction portion 421, and thus it is possible to improve the reliability of electrical connection. If the aspect ratio is equal to or more than 0.1, it is possible to prevent the wiring portion 415 from being deformed toward the +Z side due to pressing force from the first conduction portion 421 and thus the first conduction portion 421 from coming close to the ultrasonic transducer 45.

Here, the first conduction portion 421 is in pressure contact with the wiring portion 415 so as to be elastically deformed. In this case, the first conduction portion 421 is deformed along the end part 415C, and is thus in close contact therewith. As mentioned above, since the first resin part 421A is elastically deformed, the first conduction portion 421 and the end part 415C can be made in close contact with each other, and thus it is possible to improve the reliability of electrical connection between the first conduction portion 421 and the wiring portion 415.

The first conductive film 421B is thinner than the first resin part 421A and, thus, does not hinder elastic deformation of the first resin part 421A. Consequently, it is possible to further improve close contact between the first conduction portion 421 and the end part 415C. Further, the stress applied to the element substrate 41 during pressure contact can be alleviated, and thus it is possible to prevent strain or damage to the element substrate 41.

The first conduction portion 421 has the curved part 421C which is curved toward the sealing plate 42 from the first connection region C1 to the outside along the XY plane. That is, the curved part 421C is curved to be separated from the piezoelectric element 413 toward +Z side. Consequently, it is possible to suppress interference between the ultrasonic transducer 45 and the first conduction portion 421.

The first conduction portion 421 having the curved part 421C can be easily formed by forming the first resin part 421A by heating, melting, and then solidifying the resin layer 53, and by coating the first resin part 421A with the first conductive film 421B.

Further, the first resin part 421A is substantially hemispherical during formation, and the end surface thereof on the inner surface 42A side is substantially circular. As the diameter $L_1$ of the end surface, the distance d1 from the sealing plate 42 to the −Z side end part Rz of the vibration range of the ultrasonic transducer 45 satisfies the above Expression (1). Consequently, the first conduction portion 421 can be disposed outside the vibration range of the ultrasonic transducer 45, and thus it is possible to further suppress interference between the ultrasonic transducer 45 and the first conduction portion 421. Therefore, it is possible to appropriately drive the ultrasonic transducer 45.

In the embodiment, the second conduction portion 424 is in contact with the electrical connection portion 416C having a smaller height dimension (height) than that of the wiring portion 415 that is in contact with the first conduction portion 421. Consequently, it is possible to perform the wiring connection using the second conduction portion 424 that is larger than the first conduction portion 421 in the wiring region Ar2. Therefore, it is possible to increase an area of the second connection region C2 between the second conduction portion 424 and the electrical connection portion 416C, and thus it is possible to reduce the contact resistance.

In the wiring region Ar2, it is easier to increase the width dimension (for example, dimensions in the X direction and the Y direction) of the electrical connection portion 416C than in the array region Ar1. Thus, the second conduction portion 424 is provided at the position of overlapping the wiring region Ar2 outside the array region Ar1, and thus it is easy to increase the size of the second conduction portion 424.

Here, the height dimension (height) of the second conduction portion 424 before the elastic deformation is substantially equal to the sum of the height dimensions (heights) of both of the wiring portion 415 and the first conduction portion 421 before the elastic deformation. In this case, the first conduction portion 421 has substantially the same deformation amount in the Z direction as that of the second conduction portion 424 that is larger than the first conduction portion 421, and thus an area of the second connection region C2 can be larger than the area of the first connection region C1. In other words, as represented by the following Expression (3), the height dimension (height) of the second conduction portion 424 before the elastic deformation is equal to or larger than the sum of the height dimensions (heights) of both of the wiring portion 415 and the first conduction portion 421, and thus the area of the second connection region C2 can be larger than the area of the first connection region C1. Therefore, it is possible to reduce resistance in a connection part of the second conduction portion 424, and thus a higher current can flow. It is possible to reduce the number of second conduction portions 424, and thus it is possible to simplify the configuration thereof.

Expression 2: $L_2/2 \geq L_3 + L_1/2$ (3)

The height dimension (height) of the second conduction portion 424 before the elastic deformation may be smaller than the sum of the height dimensions (heights) of both of the wiring portion 415 and the first conduction portion 421 before the elastic deformation. In this case, the deformation amount of the first conduction portion 421 in the Z direction is larger than that of the second conduction portion 424, and thus the area of the first connection region C1 can be substantially the same as the area of the end part 415C of the wiring portion 415 or the first connection region C1 can cover the end part 415C of the wiring portion 415. In other words, as represented by the following Expression (4), the height dimension (height) of the second conduction portion 424 before the elastic deformation is equal to or smaller than the sum of the height dimensions (heights) of both of the wiring portion 415 and the first conduction portion 421, and thus the area of the first connection region C1 can be equal to or larger than the area of the end part 415C of the wiring portion 415. Therefore, it is possible to reduce resistance in a connection part of the first conduction portion 421, and thus a higher current can flow.

Expression 3: $L_2/2 < L_3 + L_1/2$ (4)

In the embodiment, the second bonding part 417B bonds the element substrate 41 to the sealing plate 42 in the array region Ar1. In this configuration, for example, the uniformity of a distance between the element substrate 41 and the sealing plate 42 can be improved compared with a configuration in which the element substrate 41 and the sealing plate 42 are bonded to each other by using only the first bonding part 417A. Consequently, for example, it is possible to prevent defective connection between the first conduction portion 421 and the wiring portion 415 from occurring due to warping or the like of the element substrate 41 in the central part of the array region Ar1. Therefore, it is possible to improve the reliability of wiring connection between the element substrate 41 and the sealing plate 42.

Second Embodiment

Hereinafter, a second embodiment will be described.

In the first embodiment, the first conduction portion 421 has a substantially hemispherical conduction part with the wiring portion 415 and is provided to overlap the wiring portion 415 in plan view in the Z direction. In contrast, the second embodiment is mainly different from the first embodiment in that a wiring portion and a first conduction portion are provided to intersect each other in plan view in the Z direction.

In the following description, the same constituent elements as those in the first embodiment are given the same reference numerals, and description thereof will be omitted or will be made briefly.

Configuration of Ultrasonic Device

Figure 13:
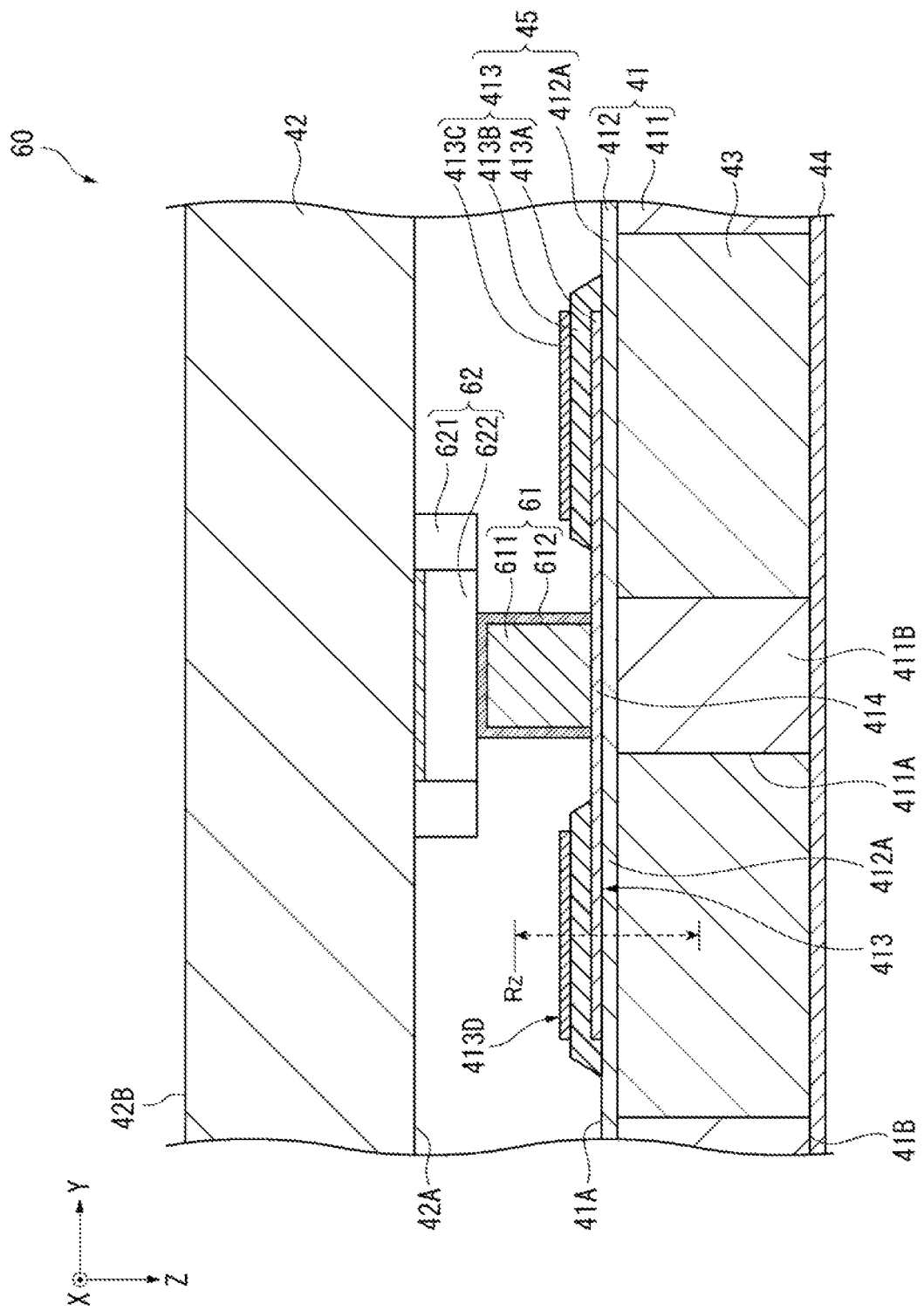
FIG. 13 is a sectional view showing a schematic configuration of main portions of an ultrasonic device according to a second embodiment.
Figure 14:
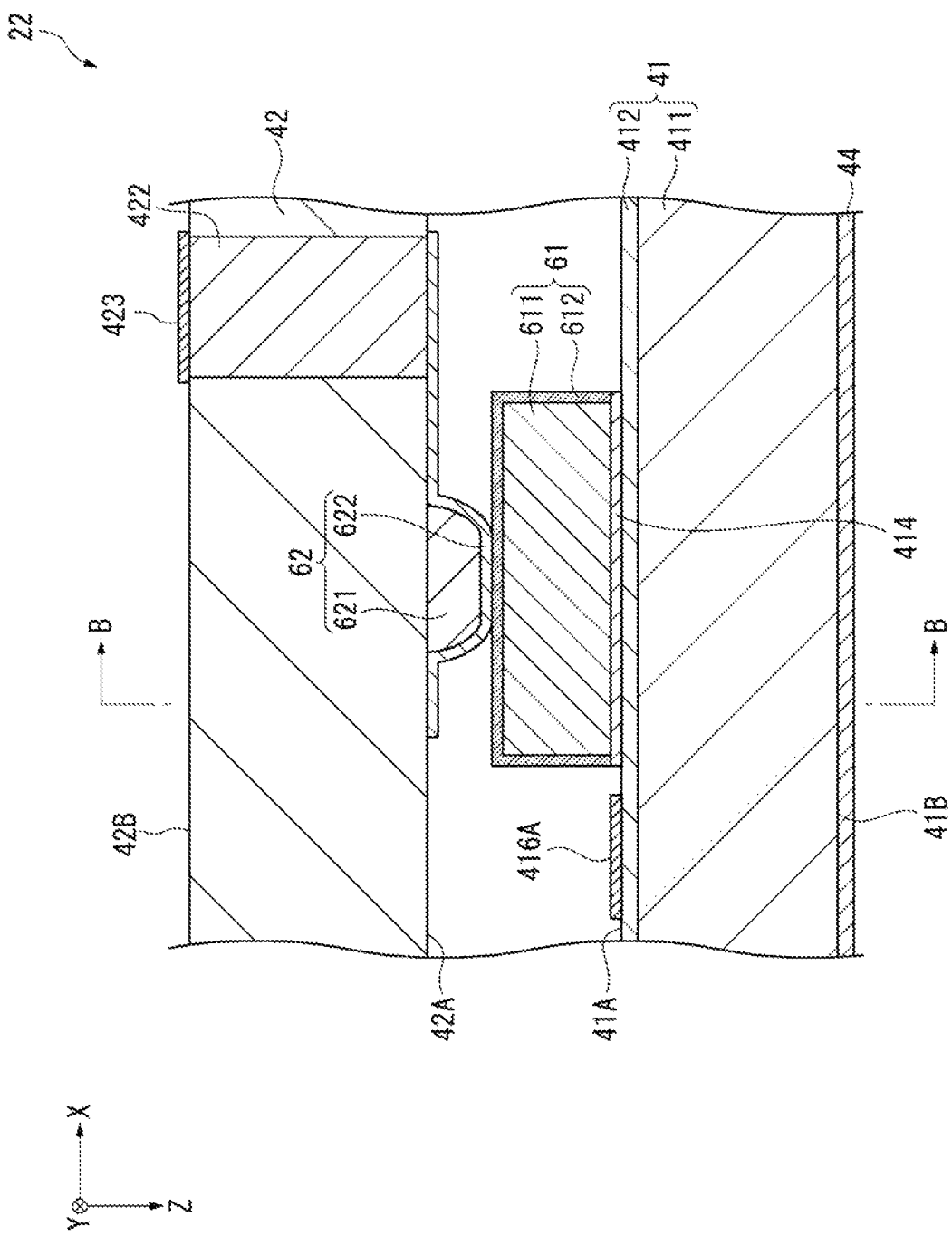
FIG. 14 is a sectional view showing a schematic configuration of main portions of the ultrasonic device according to the second embodiment.
Figure 15:
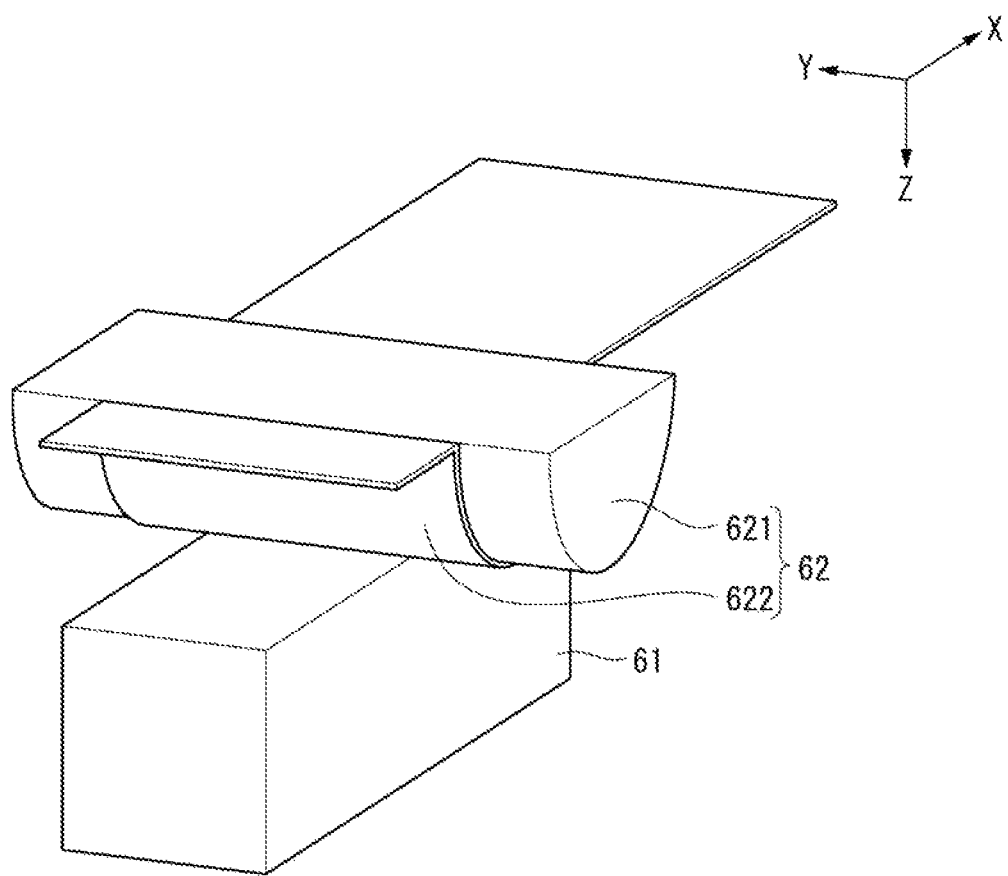
FIG. 15 is a perspective view showing a schematic configuration of main portions of the ultrasonic device according to the second embodiment.

FIG. 13 is a sectional view showing a schematic configuration of main portions of an ultrasonic device according to the second embodiment. FIG. 14 is a sectional view showing a schematic configuration of main portions of the ultrasonic device according to the second embodiment in FIG. 13. FIG. 15 is a perspective view showing a wiring portion and a first conduction portion of the ultrasonic device according to the second embodiment. FIG. 13 is a sectional view of an ultrasonic device 22 taken along the line B-B in FIG. 14.

As shown in FIGS. 13 and 14, a wiring portion 61 is provided on the element substrate 41 in the ultrasonic device 60 of the second embodiment. A first conduction portion 62 is provided on the sealing plate 42. The wiring portion 61 and the first conduction portion 62 are in contact with and electrically connected to each other. Consequently, the lower electrode 413A of the piezoelectric element 413 of the ultrasonic transducer 45 is electrically connected to the circuit substrate 23 via the wiring portion 61, the first conduction portion 62, the first through-electrode 422, the lower electrode wire 423, and the like.

As shown in FIG. 14, in the second embodiment, a configuration in which a single first through-electrode 422 is provided for a single first conduction portion 62 is exemplified, but the number or an arrangement position of the first through-electrodes 422 is not limited to the configuration in the second embodiment.

Configuration of Wiring Portion

The wiring portion 61 includes a main body part 611 and a coating part 612 and has conductivity. The wiring portion 61 is configured in the substantially same manner as the wiring portion 415 of the first embodiment except that the X direction is a longitudinal direction.

Above all, the coating part 612 which is formed by using a conductive metal material is configured in the substantially same manner as the coating part 415B of the first embodiment and is formed to cover a surface of the main body part 611.

The main body part 611 is provided at a position overlapping the wall portion 411B such that the X direction is a longitudinal direction thereof. In the main body part 611, for example, a dimension thereof in the X direction is substantially the same as that of the opening 411A, and a dimension thereof in the Y direction is slightly smaller than that of the wall portion 411B. More specifically, the main body part 611 has, for example, a dimension of 30 μm in the X direction, a dimension (width dimension) of 10 μm in the Y direction, and a dimension (height dimension) of 10 μm in the Z direction.

Similar to the first embodiment, the main body part 611 is formed, for example, on the lower electrode connection line 414 according to an electroplating method by using a conductive metal material. In other words, in the second embodiment, a dimension of the lower electrode connection line 414 in the X direction is substantially the same as that of the opening 411A.

Configuration of First Conduction Portion

A longitudinal direction of the first conduction portion 62 is the Y direction, and the first conduction portion 62 is provided on the inner surface 42A of the sealing plate 42 so as to intersect the wiring portion 61 in plan view in the Z direction (refer to FIG. 15). The first conduction portion 62 includes a first resin part 621 and a first conductive film 622 which covers at least a part of the first resin part 621 and is electrically connected to the first through-electrode 422. The first conduction portion 62 is in pressure and close contact with the wiring portion 61 provided on the element substrate 41 and is electrically connected to the wiring portion 61.

The first resin part 621 is formed by using an elastic resin material in the same manner as in the first embodiment. In the second embodiment, the first resin part 621 has the Y direction as a longitudinal direction and is formed in a substantially semi-cylindrical shape in which a ZX section before being elastically deformed is substantially semi-circular. The ZX section of the first resin part 621 is not limited to being substantially semi-circular and may be substantially trapezoidal (a state in which corners of a trapezoid are rounded).

The first conductive film 622 is provided to stride over the first resin part 621 along the X direction by using the same conductive material as that in the first embodiment. Specifically, the first conductive film 622 is provided at a position overlapping at least the wiring portion 61 on the first resin part 621. On the first resin part 621, a dimension of the first conductive film 622 in the Y direction is larger than a dimension of the wiring portion 61. A +X side end part of the first conductive film 622 extends to a position overlapping the +Z side end part of the first through-electrode 422 and is electrically connected to the first through-electrode 422.

The first conduction portion 62 configured as mentioned above is in pressure contact with the −Z side end part of the wiring portion 61. In this case, the first conduction portion 62 is in close contact with the wiring portion 61 by elastic force. As mentioned above, the wiring portion 61 and the first conduction portion 62 can be made in close contact with each other by the elastic force of the first conduction portion 62, and thus it is possible to improve the connection reliability between the wiring portion 61 and the first conduction portion 62. As shown in FIG. 13, the end part of the first conduction portion 62 on the +Z side is located further toward the sealing plate 42 side than the −Z side end part Rz of the vibration range of the ultrasonic transducer 45. Thus, interference between the first conduction portion 62 and the ultrasonic transducer 45 is suppressed. Similar to the first embodiment, the first conductive film 622 is sufficiently thinner than the first resin part 621 in thickness. Consequently, the first conductive film 622 can be deformed according to elastic deformation of the first resin part 621.

Advantageous Effects of Second Embodiment

The wiring portion 61 and the first conduction portion 62 intersect each other in plan view in the Z direction. Consequently, in the ultrasonic device 60, a position difference between the element substrate 41 and the sealing plate 42 is allowable during wiring connection, and thus it is possible to prevent defective connection from occurring. In other words, in the plan view, in a case where the wiring portion 61 and the first conduction portion 62 do not intersect each other (for example, a case where the wiring portion 61 and the first conduction portion 62 are parallel to each other or a connection surface between the wiring portion 61 and the first conduction portion 62 is substantially rectangular or substantially circular), an area of a connection part may be reduced due to a position difference between the element substrate 41 and the sealing plate 42, so that contact resistance increases. Appropriate electrical connection may not be performed due to a position difference. In contrast, since the wiring portion 61 and the first conduction portion 62 are disposed to intersect each other, an allowable amount for a position difference in the X direction and the Y direction during alignment can be increased (refer to FIG. 15). Thus, alignment between the element substrate 41 and the sealing plate 42 can be easily performed, and wiring connection can also be easily performed. It is possible to improve connection reliability.

The wiring portion 61 has the X direction (second direction) as a longitudinal direction, and the first conduction portion 62 has the Y direction as a longitudinal direction. In the Y direction (third direction), a dimension of the first conductive film 622 of the first conduction portion is larger than a dimension of the wiring portion 61. Consequently, even if a position difference between the element substrate 41 and the sealing plate 42 occurs in the Y direction during wiring connection, it is possible to maintain connection reliability on the basis of elastic force while allowing the position difference.

Modification Example

The present invention is not limited to the above-described embodiments, and configurations obtained through modifications, alterations, and combinations of the respective embodiments as appropriate within the scope capable of achieving the object of the present invention are included in the present invention.

For example, in the first embodiment, as an example, a description has been made of a configuration in which wiring connection between the element substrate 41 and the sealing plate 42 is performed by using the wiring portion 415 provided on the element substrate 41 and the first conduction portion 421 provided on the sealing plate 42. However, the present invention is not limited to the configuration of each embodiment and may employ a configuration in each modification example which will be described below. A modification example of the first embodiment will be exemplified as each modification example which will be described below, and the same modification may also be applied to the second embodiment.

First Modification Example

Figure 16:
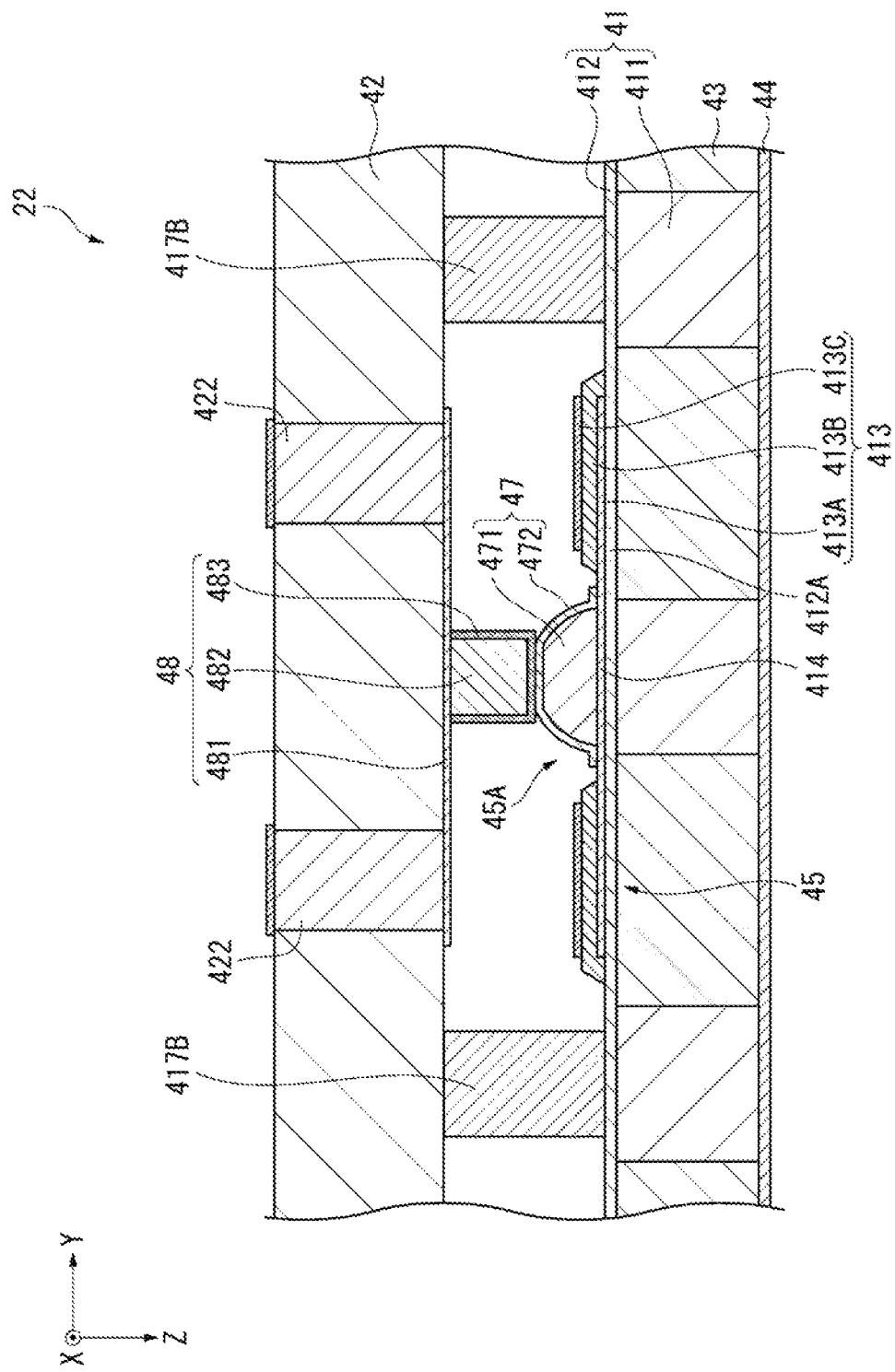
FIG. 16 is a sectional view showing a schematic configuration of an ultrasonic device according to a first modification example.

FIG. 16 is a sectional view showing a schematic configuration of the ultrasonic device 22 according to a first modification example.

As shown in FIG. 16, in the first modification example, a wiring portion 47 which is configured in the same manner as the first conduction portion 421 of the first embodiment is provided on the element substrate 41. A first conduction portion 48 which is configured in the same manner as the wiring portion 415 of the first embodiment is provided on the sealing plate 42. The wiring portion 47 and the first conduction portion 48 are in contact with and electrically connected to each other.

The wiring portion 47 includes a resin part 471, and a conductive film 472 which covers the resin part 471. The resin part 471 is configured in the same manner as the first resin part 421A and is formed on the rear surface 41A of the element substrate 41. The conductive film 472 is configured in the same manner as the first conductive film 421B and is conductively connected to the lower electrode 413A of each ultrasonic transducer 45 forming the ultrasonic transducer group 45A.

The first conduction portion 48 includes a connection line 481 extracted from the first through-electrode 422, a main body part 482 provided on the connection line 481, and a coating part 483 coating the main body part 482. The connection line 481 which is configured in the same manner as the lower electrode connection line 414 connects the first through-electrode 422 to the first conduction portion 48 and is a base layer of the main body part 482 in the modification example. The main body part 482 and the coating part 483 are configured in the same manner as the main body part 415A and the coating part 415B described above, respectively.

Also in the first modification example, a height dimension (height) of the wiring portion 47 is larger than a height dimension (height) of the piezoelectric element 413. Consequently, similar to the first embodiment, it is possible to suppress interference between the wiring portion 47 and the ultrasonic transducer 45, and thus it is possible to easily perform wiring connection. An end part of the wiring portion 47 on the −Z side is preferably located further toward the sealing plate 42 side than the −Z side end of the drive range of the ultrasonic transducer 45.

Since the wiring portion 47 is elastically deformed, close contact with the first conduction portion 48 can be improved, and the stress applied to the element substrate 41 and the sealing plate 42 during connection can be alleviated.

Second Modification Example

Figure 17:
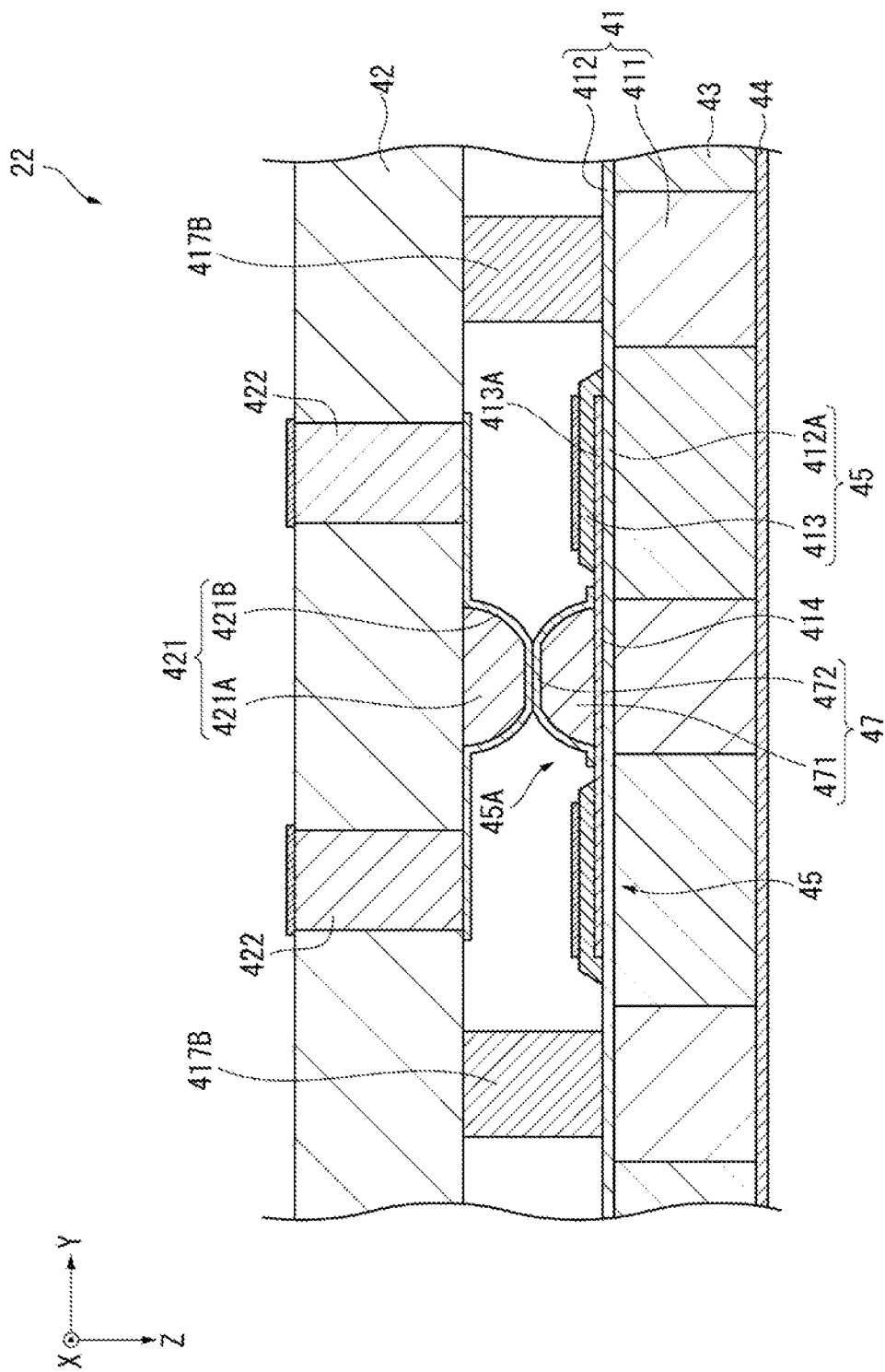
FIG. 17 is a sectional view showing a schematic configuration of an ultrasonic device according to a second modification example.

FIG. 17 is a sectional view showing a schematic configuration of the ultrasonic device 22 according to a second modification example.

As shown in FIG. 17, in the second modification example, the wiring portion 47 of the first modification example is provided on the element substrate 41, and the wiring portion 47 and the first conduction portion 421 provided on the sealing plate 42 are in contact with and electrically connected to each other.

Also in this configuration, similar to the first embodiment, it is possible to suppress interference between the wiring portion 47 and the ultrasonic transducer 45, and thus it is possible to easily perform wiring connection. Since the wiring portion 47 and the first conduction portion 421 are elastically deformed, close contact between the wiring portion 47 and the first conduction portion 48 can be improved, and the stress applied to the element substrate 41 and the sealing plate 42 during connection can be alleviated.

Since both of the wiring portion 47 and the first conduction portion 421 are elastically deformed, it is possible to further improve close contact between the wiring portion 47 and the first conduction portion 48.

Third Modification Example

Figure 18:
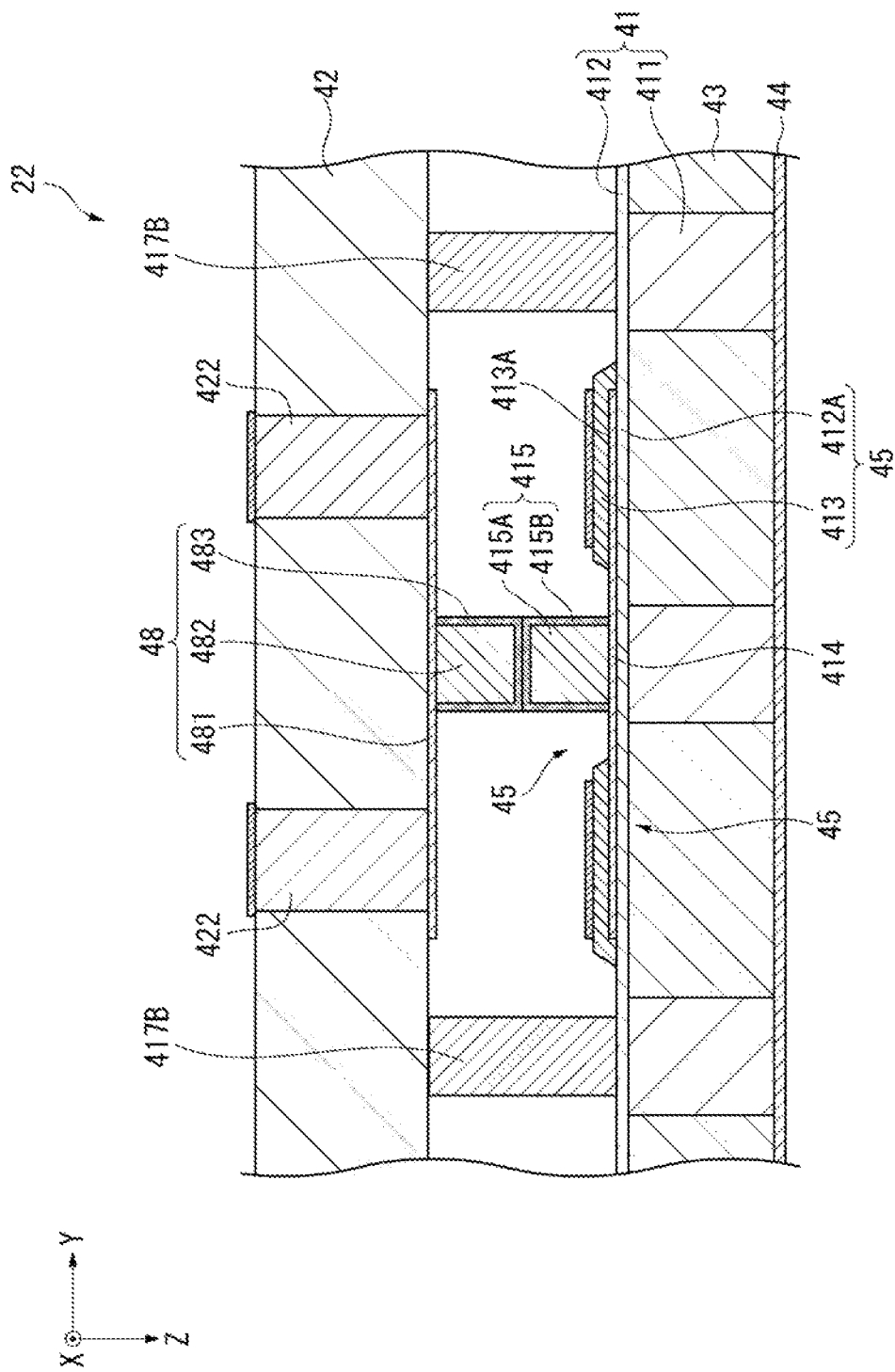
FIG. 18 is a sectional view showing a schematic configuration of an ultrasonic device according to a third modification example.

FIG. 18 is a sectional view showing a schematic configuration of the ultrasonic device 22 according to a third modification example.

As shown in FIG. 18, in the third modification example, the first conduction portion 48 of the first modification example is provided on the sealing plate 42, and the first conduction portion 48 and the wiring portion 415 provided on the element substrate 41 are in contact with and electrically connected to each other.

In this configuration, similar to the first embodiment, it is possible to suppress interference between the first conduction portion 48 and the ultrasonic transducer 45, and thus it is possible to easily perform wiring connection.

It is possible to adjust a distance between the element substrate 41 and the sealing plate 42 according to height dimensions (heights) of the wiring portion 415 and the first conduction portion 48. Further, surfaces of the wiring portion 415 and the first conduction portion 48 are bonded to each other through diffusion bonding as described above, so that the element substrate 41 and the sealing plate 42 can be bonded to each other at a plurality of positions in the array region Ar1, and thus it is possible to improve the in-plane uniformity of a distance between the element substrate 41 and the sealing plate 42.

Fourth Modification Example

Figure 19:
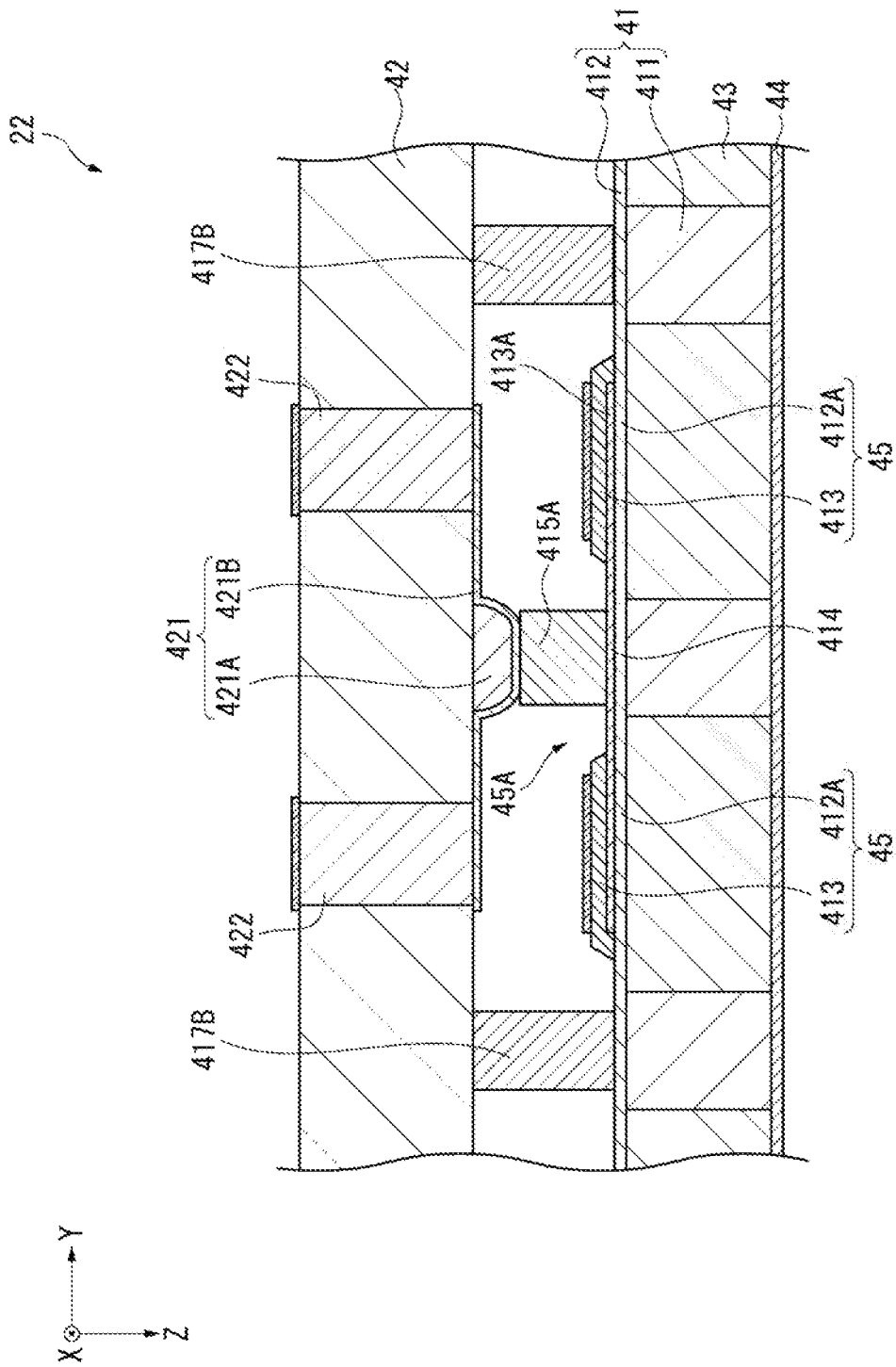
FIG. 19 is a sectional view showing a schematic configuration of an ultrasonic device according to a fourth modification example.

FIG. 19 is a sectional view showing a schematic configuration of the ultrasonic device 22 according to a fourth modification example.

As shown in FIG. 19, in the fourth modification example, the main body part 415A of the first embodiment as a wiring portion is provided on the element substrate 41, and the main body part 415A and the first conduction portion 421 provided on the sealing plate 42 are in contact with and electrically connected to each other.

In this configuration, similar to the first embodiment, it is possible to suppress interference between the first conduction portion 421 and the ultrasonic transducer 45, and thus it is possible to easily perform wiring connection. The coating part 415B is not formed, and thus a manufacturing process can be simplified.

Even in a case where bonding cannot be performed through diffusion bonding between the main body part 415A and the first conduction portion 421, the second bonding parts 417B are disposed with a bonding position interposed therebetween, and thus it is possible to improve the reliability of wiring connection.

Fifth Modification Example

Figure 20:
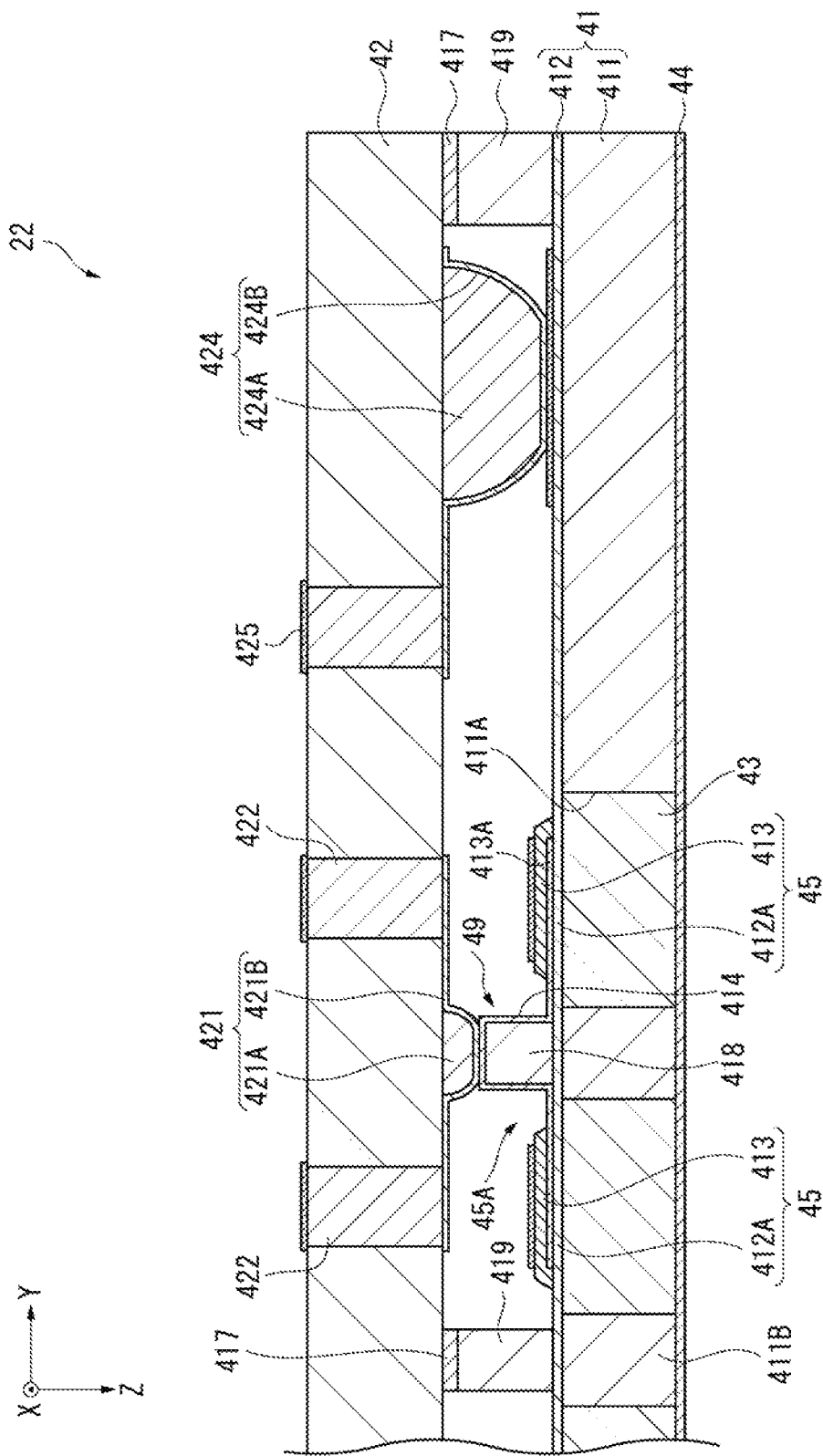
FIG. 20 is a sectional view showing a schematic configuration of an ultrasonic device according to a fifth modification example.
Figure 21:
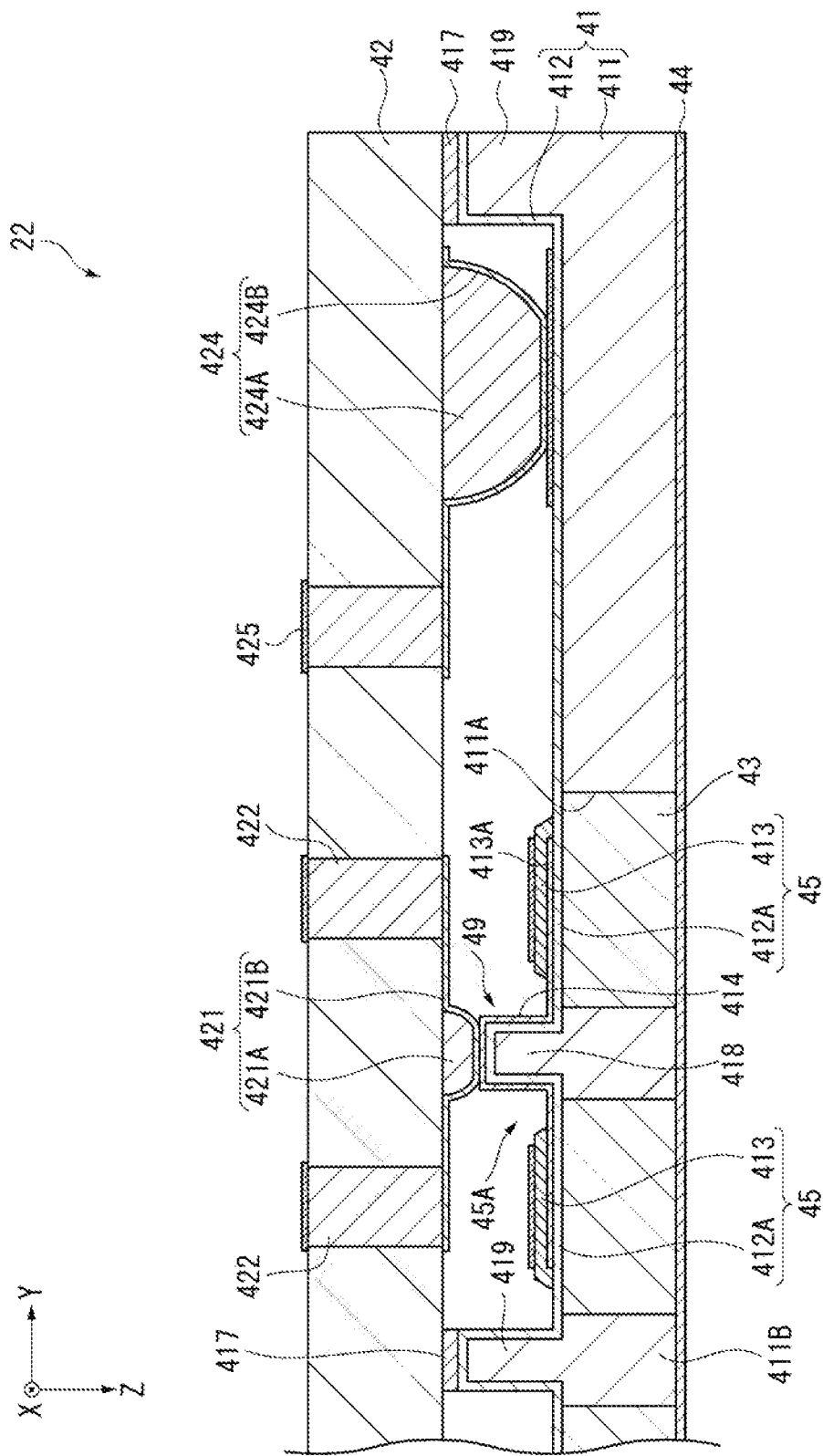
FIG. 21 is a sectional view showing a schematic configuration of the ultrasonic device according to the fifth modification example.

FIGS. 20 and 21 are sectional views showing schematic configurations of the ultrasonic device 22 according to a fifth modification example.

As shown in FIG. 20, in the fifth modification example, the element substrate 41 is provided with a wiring portion 49 instead of the wiring portion 415 of the first embodiment, and the wiring portion 49 and the first conduction portion 421 provided on the sealing plate 42 are in contact with and electrically connected to each other. Also in this configuration, similar to the first embodiment, it is possible to suppress interference between the first conduction portion 421 and the ultrasonic transducer 45, and thus it is possible to easily perform wiring connection.

A first projecting portion 418 projecting toward the sealing plate 42 side is provided at a position that is opposite to the first conduction portion 421 on the substrate main body 411. The lower electrode connection line 414 is provided to stride over the first projecting portion 418. The wiring portion 49 is formed of the first projecting portion 418 and a part of the lower electrode connection line 414. For example, the first projecting portion 418 is made of the same material as that of the substrate main body 411 and is bonded onto the vibration film 412. In the modification example, the lower electrode connection line 414 may be formed by laminating a TiW layer (50 nm) and an Au layer (100 nm) in this order. As mentioned above, the Au layer is formed on the surface of the wiring portion 49, and thus the first conduction portion 421 having an Au layer on the surface thereof and the wiring portion 49 can be bonded to each other through diffusion bonding.

A second projecting portion 419 is provided at a formation position of the bonding portion 417 on the substrate main body 411. The second projecting portion 419 is formed in the same manner as the first projecting portion 418 and projects toward the sealing plate 42 side. The bonding portion 417 is formed on a surface of the second projecting portion 419 on the sealing plate 42 side.

There may be a configuration in which the first conduction portion 48 of the first modification example is provided instead of the first conduction portion 421. The second projecting portion 419 is formed, and thus a bonding height between the substrate main body 411 and the sealing plate 42 can be easily determined.

As shown in FIG. 21, the first projecting portion 418 and the second projecting portion 419 may be formed by adjusting an etching amount, for example, when the rear surface 41A side of the substrate main body 411 is formed through etching. In this case, for example, the rear surface 41A side of the substrate main body 411 is etched such that the first projecting portion 418 and the second projecting portion 419 are formed, and then the vibration film 412 is formed. Next, the operation surface 41B side of the substrate main body 411 is etched, and thus the opening 411A is formed.

In the fifth modification example, the first projecting portion 418 and the second projecting portion 419 are formed by etching the substrate main body 411, but, for example, the second projecting portion 419 may be formed on the sealing plate 42. The second projecting portion 419 is formed according to the same method as that of the first projecting portion 418 and projects toward the substrate main body 411 side. The bonding portion 417 is formed on a surface of the second projecting portion 419 on the substrate main body side. The second projecting portion 419 is formed as mentioned above, and thus the substrate main body 411 can be more easily formed than in a case where the first projecting portion 418 and the second projecting portion 419 are formed on the substrate main body 411. As described above, a bonding height between the substrate main body 411 and the sealing plate 42 can be easily determined.

Other Modification Examples

FIGS. 22 to 26 are sectional views showing schematic configurations of ultrasonic devices 22 according to other modification examples.

In the above-described respective embodiments and modification examples, the second bonding parts 417B are disposed with each wiring portion interposed therebetween in one direction in the array region Ar1, but this is only an example.

Figure 22:
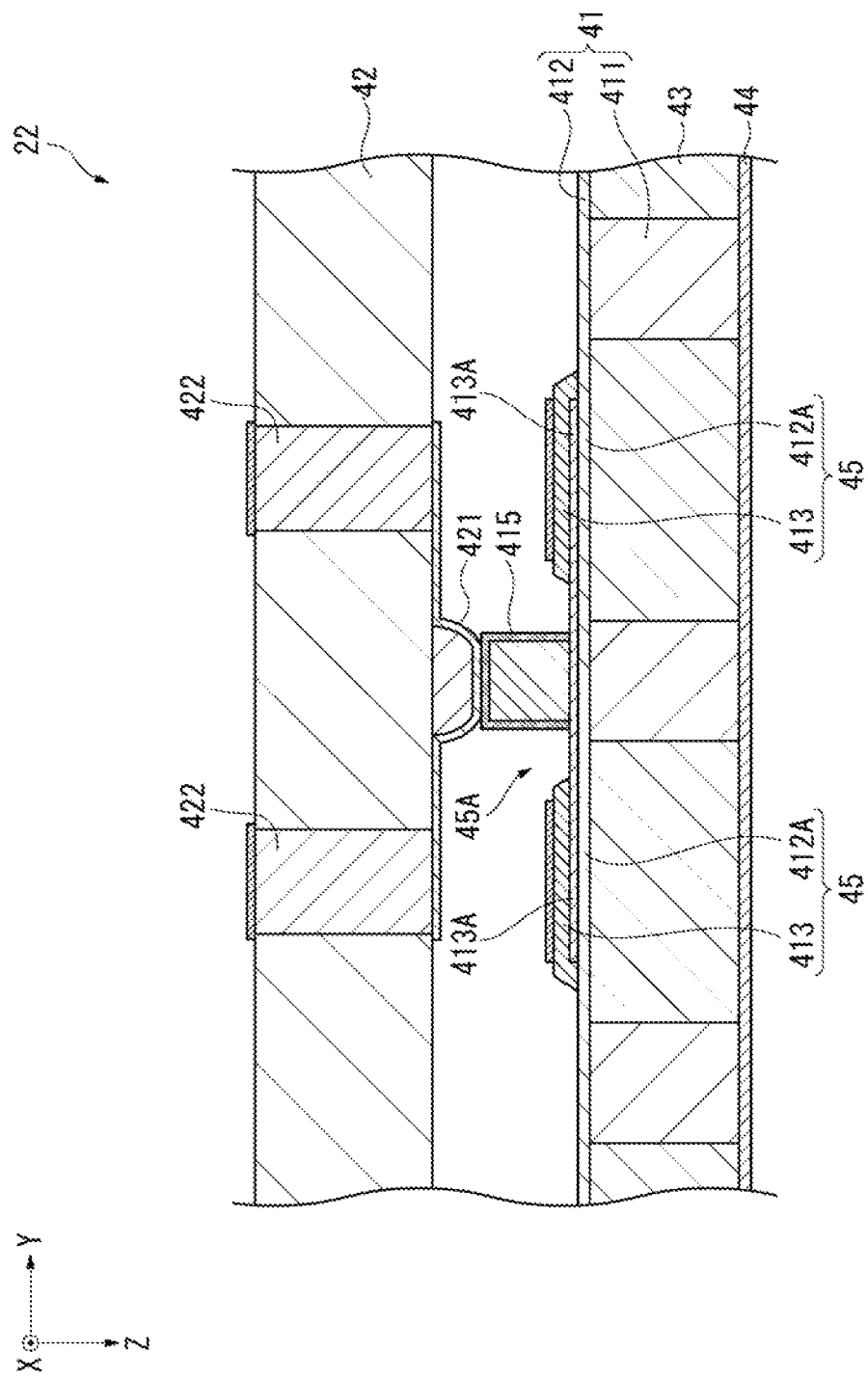
FIG. 22 is a sectional view showing a schematic configuration of an ultrasonic device according to another modification example.
Figure 23:
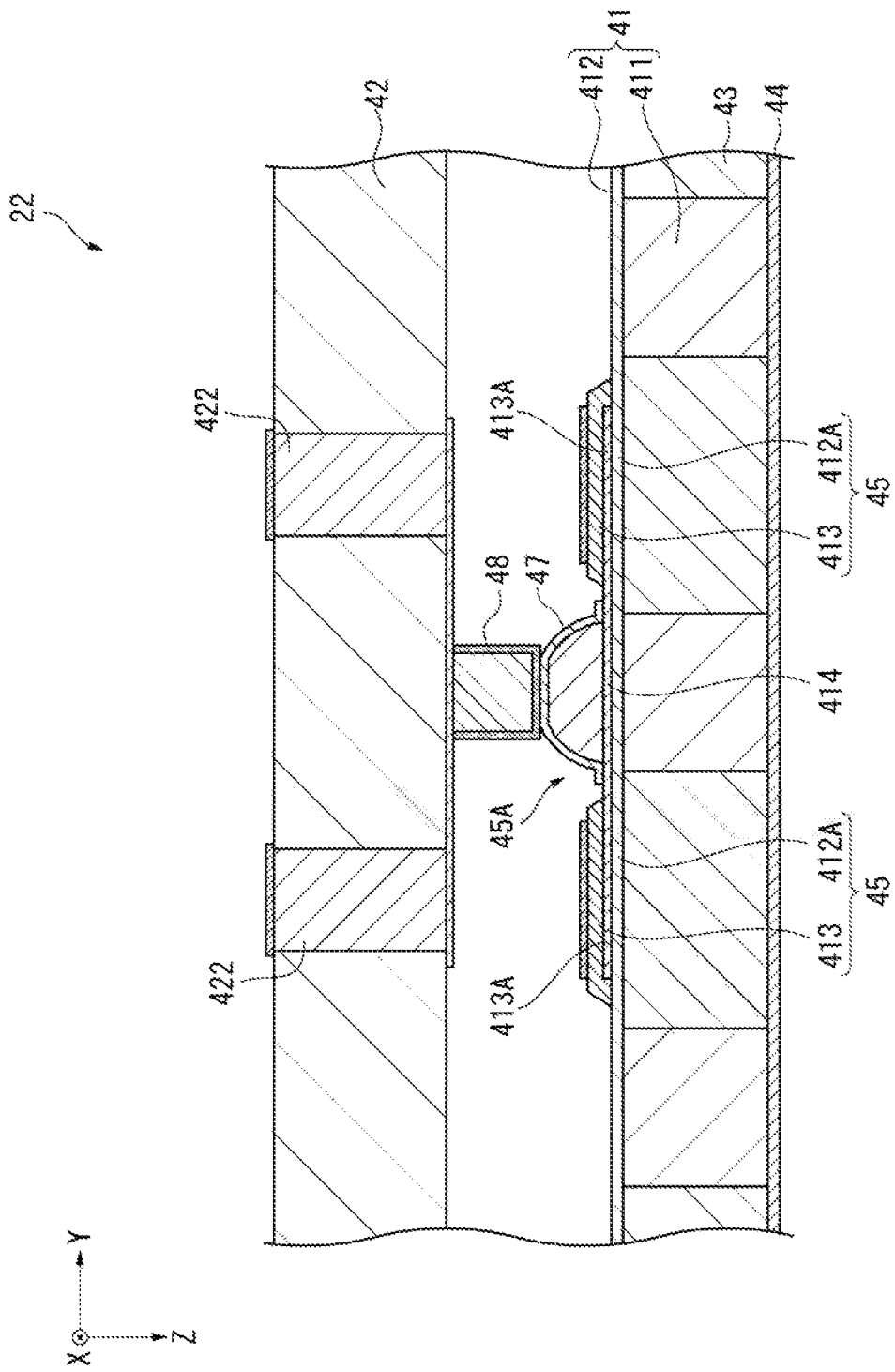
FIG. 23 is a sectional view showing a schematic configuration of an ultrasonic device according to still another modification example.
Figure 24:
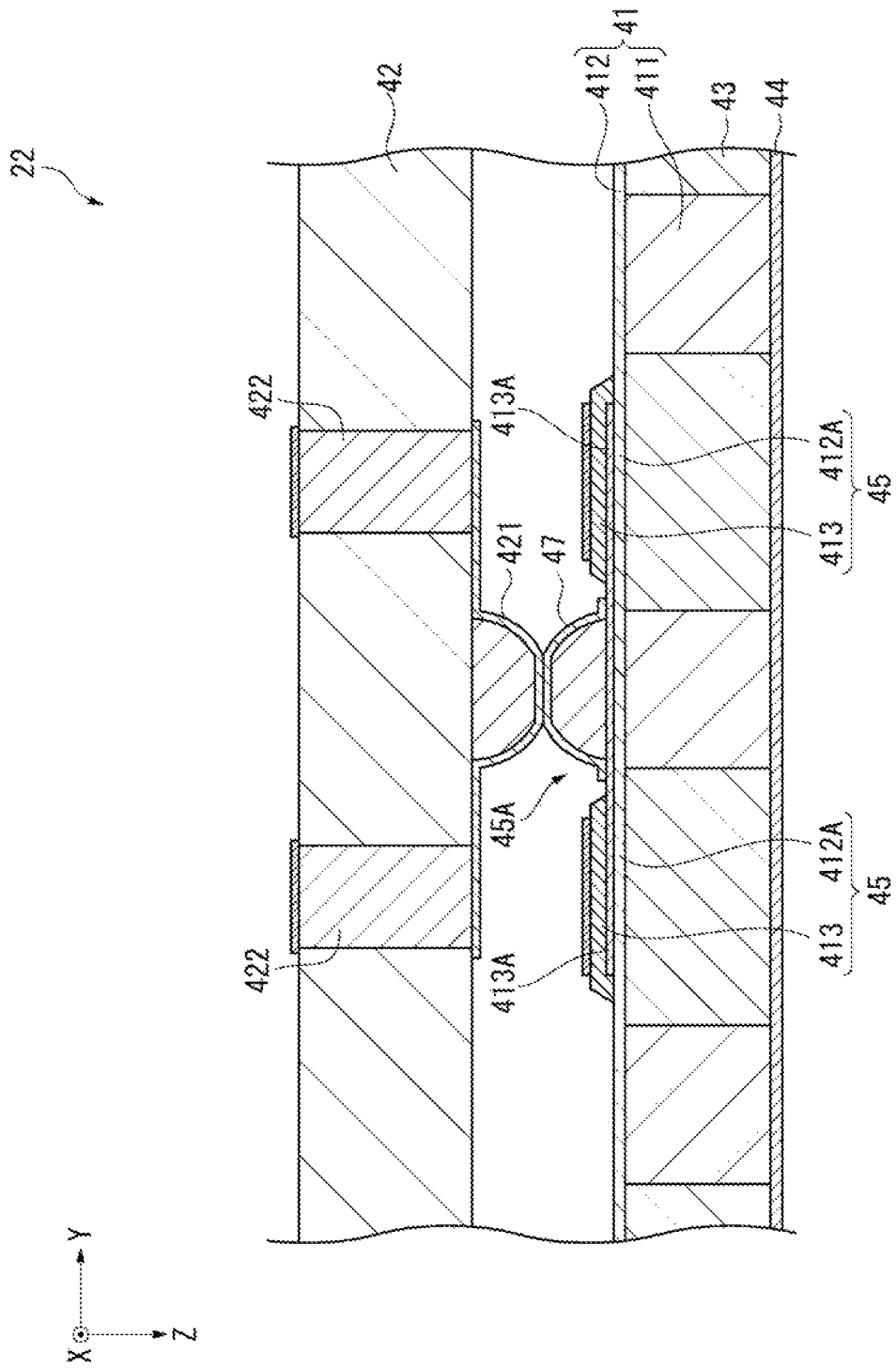
FIG. 24 is a sectional view showing a schematic configuration of an ultrasonic device according to still another modification example.
Figure 25:
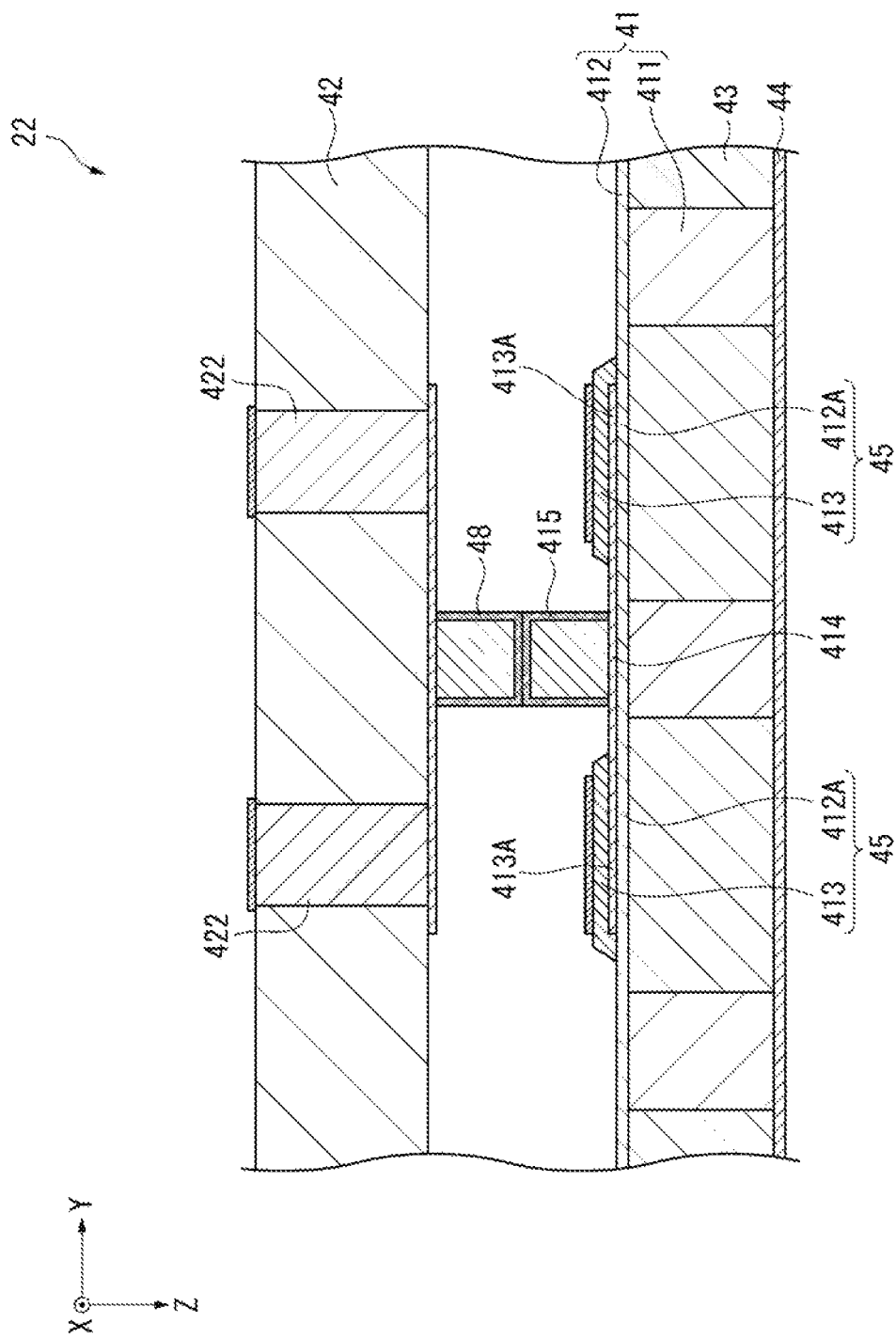
FIG. 25 is a sectional view showing a schematic configuration of an ultrasonic device according to still another modification example.
Figure 26:
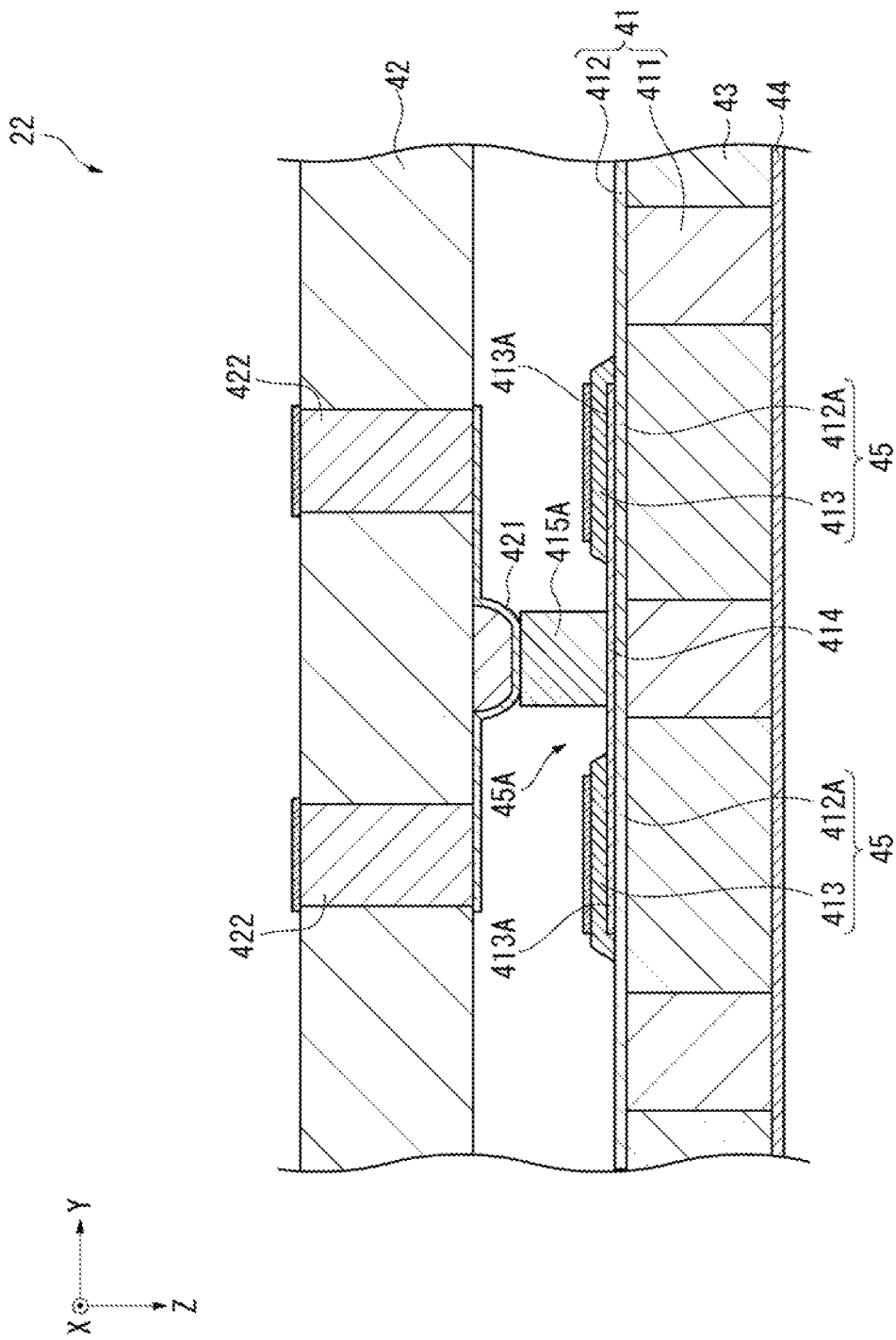
FIG. 26 is a sectional view showing a schematic configuration of an ultrasonic device according to still another modification example.

FIG. 22 shows a modification example of the first embodiment, and FIGS. 23 to 26 show respective modification examples of the first to fourth modification examples. As shown in FIGS. 22 to 26, for example, the second bonding part 417B may not be provided in the array region Ar1. In this case, the element substrate 41 and the sealing plate 42 are bonded to each other via the first bonding part 417A. Even in this configuration, the element substrate 41 and the sealing plate 42 have the sufficient rigidity, and thus it is possible to secure the connection reliability between the wiring portion and the first conduction portion. In a case where it is possible to perform diffusion bonding between the wiring portion and the first conduction portion, it is possible to improve connection reliability, and it is also possible to simplify a configuration due to the second bonding part 417B not being provided.

A pair of the second bonding parts 417B may be disposed for some of the wiring portions disposed in the array region Ar1. Not only a configuration in which two second bonding parts 417B are disposed with the wiring portion interposed therebetween but also a configuration in which a single second bonding part 417B is disposed may be employed. For example, the second bonding part 417B may be disposed on the +Y side or the −Y side of each wiring portion.

In the above-described respective embodiments, the first conduction portion and the second conduction portion have a configuration in which the resin part is coated with the conductive film thinner than the resin part, but any other configuration may be used. For example, there may be a configuration in which a conductive layer having the substantially same thickness as that of the resin part is laminated on the resin part, and the conductive layer may be thicker than the resin part. If the resin part is thicker than the conductive layer, it is possible to further alleviate the stress applied to the element substrate 41 or the sealing plate 42 due to elasticity of the first conduction portion and the second conduction portion.

In the first embodiment, the first conduction portion 421 includes the curved part 421C, but is not limited thereto, and may include an inclined part which is inclined in a direction of becoming distant from the piezoelectric element 413 toward the element substrate 41 from the sealing plate 42. This inclined part may have a planar or curved inclined surface and may have an inclined surface including a planar surface and a curved surface.

In the above-described respective embodiments, the ultrasonic transducer group 45A formed of two ultrasonic transducers 45 is used as a single transmission/reception channel, but the ultrasonic transducer group 45A may be formed by connecting the lower electrodes 413A of three or more ultrasonic transducers 45 to each other. There may be a configuration in which the lower electrodes 413A of the respective ultrasonic transducers 45 are separate from each other, and thus each of the ultrasonic transducers 45 is individually driven. In this case, each ultrasonic transducer 45 may function as a single transmission/reception channel.

In the above-described respective embodiments, a description has been made of an example of the ultrasonic device 22 having a two-dimensional array structure in which the ultrasonic transducer groups 45A each functioning as a single transmission/reception channel are disposed in a matrix in the array region Ar1 of the element substrate 41, but this is only an example. For example, the ultrasonic device may have a one-dimensional array structure in which a plurality of transmission/reception channels are disposed along one direction. For example, the ultrasonic transducer group 45A may be formed of a plurality of ultrasonic transducers 45 disposed along the X direction, and a plurality of ultrasonic transducer groups 45A are disposed in the Y direction so as to form the ultrasonic array AL having a one-dimensional array structure.

In the above-described embodiments, a description has been made of an example of a configuration in which the ultrasonic transducer 45 is formed of the vibration film 412 and the piezoelectric element 413 formed on the vibration film 412, but this is only an example. For example, the ultrasonic transducer 45 may be configured to include a flexible film, a first electrode provided on the flexible film, and a second electrode provided at a position opposing the first electrode in a sealing plate. The first electrode and the second electrode form an electrostatic actuator as a vibrator. In this configuration, an ultrasonic wave can be transmitted by driving the electrostatic actuator, and an ultrasonic wave can be detected by detecting electrostatic capacitance between the electrodes.

In the above-described respective embodiments, an ultrasonic apparatus which measures an organ of a living body has been described as an example of an electronic apparatus, but the invention is not limited thereto. For example, the configurations of the above-described respective embodiments and modification examples may be applied to a measurement apparatus which measures various structural bodies, detects a defect of the structural body, or inspects aging thereof. The same is true of a measurement apparatus which measures, for example, a semiconductor package or a wafer and detects a defect of such a measurement target.

In the above-described embodiments, a description has been made of an example of a configuration in which the ultrasonic transducer is provided on the element substrate, but the invention is not limited thereto. For example, the configurations of the respective embodiments and modification examples may be applied to a mounting structure including a first substrate provided with an electric component such as a semiconductor IC, that is, an functional element, and a second substrate electrically connected to the first substrate, or an image display device or an image forming device in which the mounting structure is provided in a case. In other words, a wiring portion which is provided on the first substrate and is connected to the electronic component and a conduction portion which is provided on the second substrate and is connected to the wiring portion are connected to each other further toward the second substrate side than the electronic component, and thus it is possible to suppress interference between the functional element and the conduction portion and thus to appropriately and easily perform wiring connection between the first substrate and the second substrate.

A specific structure of when the present invention is implemented may be configured as appropriate by combining the respective embodiments and modification examples within the scope of being capable of achieving the object of the present invention, and may be changed to other structures as appropriate.

The invention claimed is:

1. A mounting structure comprising:
   a first substrate that has a first surface on which a functional element is provided;
   a wiring portion that is provided at a position, which is different from a position of the functional element on the first surface, and is conductively connected to the functional element;
   a second substrate that has a second surface that is opposite to the first surface; and
   a conduction portion that is provided on the second surface, is connected to the wiring portion, and is conductively connected the functional element,
   wherein the shortest distance between the functional element and the second substrate is longer than the longest distance between the second substrate and a position where the wiring portion is connected to the conduction portion, and
   wherein at least one of the wiring portion and the conduction portion includes a resin part and a conductive part covering the resin part.

2. The mounting structure according to claim 1, wherein an area of a region in which the conduction portion is bonded to the second substrate is larger than an area of a region in which the wiring portion is connected to the conduction portion.

3. The mounting structure according to claim 1, wherein, in a first direction directed from the first substrate to the second substrate, a thickness of the resin part at a position overlapping a connection region between the conduction portion and the wiring portion is larger than a thickness of the conductive part.

4. The mounting structure according to claim 1,
wherein the resin part has a substantially hemispherical shape protruding from the second surface in a case where the conduction portion is not elastically deformed, and
wherein, if the maximum diameter of an end surface of the resin part on the second substrate side is indicated by L, a distance d from the second substrate to the functional element satisfies a relationship of d>L/2.

5. The mounting structure according to claim 1,
wherein the wiring portion and the conduction portion intersect each other in plan view in a first direction directed from the first substrate to the second substrate.

6. The mounting structure according to claim 1,
wherein one of the wiring portion and the conduction portion has a second direction, which is parallel to the first surface, as a longitudinal direction,
wherein the other of the wiring portion and the conduction portion has a third direction, which is parallel to the first surface and intersects the second direction, as a longitudinal direction, and
wherein, in the second direction, a dimension of the conductive part is larger than a dimension of the other of the wiring portion and the conduction portion.

7. The mounting structure according to claim 1,
wherein the first substrate is provided with an extraction wiring that is connected to the functional element and is smaller than the wiring portion in a thickness in the first direction directed from the first substrate to the second substrate, the mounting structure further comprising:
a second conduction portion that is connected to the extraction wiring;
a second resin part that is larger than the resin part in a thickness in the first direction directed from the first substrate to the second substrate;
a second conductive part that covers the second resin part.

8. The mounting structure according to claim 1,
wherein the wiring portion is made of a metal material, and a ratio of a height of the wiring portion from the first surface in a normal direction to a width of the wiring portion on the first surface in a surface direction is 0.1 or more and 5 or less.

9. The mounting structure according to claim 1,
wherein the functional element includes a vibrator that vibrates along a first direction directed from the first substrate to the second substrate.

10. The mounting structure according to claim 9,
wherein a connection position between the wiring portion and the conduction portion is located further toward the second substrate side than a vibration range of the vibrator in the first direction.

11. The mounting structure according to claim 9,
wherein the functional element is an ultrasonic transducer including a flexible film formed on the first substrate, and the vibrator provided on the flexible film.

12. The mounting structure according to claim 1, further comprising:
a bonding portion that bonds the first substrate to the second substrate,
wherein the first substrate has a functional region in which a plurality of the functional elements are formed, and
wherein the bonding portion bonds the first substrate to the second substrate in the functional region.

13. An ultrasonic device comprising:
a first substrate that has a first surface on which a vibrator is provided;
a wiring portion that is provided at a position, which is different from a position of the vibrator on the first surface, and is conductively connected to the vibrator;
a second substrate that has a second surface that is opposite to the first surface; and
a conduction portion that is provided on the second surface, is connected to the wiring portion, and is conductively connected to the vibrator,
wherein the shortest distance between the vibrator and the second substrate is longer than the longest distance between the second substrate and a position where the wiring portion is connected to the conduction portion, and
wherein at least one of the wiring portion and the conduction portion includes a resin part and a conductive part covering the resin part.

14. An ultrasonic probe comprising:
a first substrate that has a first surface on which a vibrator is provided;
a wiring portion that is provided at a position, which is different from a position of the vibrator on the first surface, and is conductively connected to the vibrator;
a second substrate that has a second surface that is opposite to the first surface;
a conduction portion that is provided on the second surface, is connected to the wiring portion, and is conductively connected the vibrator; and
a case in which the first substrate, the wiring portion, the second substrate, and the conduction portion are stored,
wherein the shortest distance between the vibrator and the second substrate is longer than the longest distance between the second substrate and a position where the wiring portion is connected to the conduction portion, and
wherein at least one of the wiring portion and the conduction portion includes a resin part and a conductive part covering the resin part.

15. An ultrasonic apparatus comprising:
a first substrate that has a first surface on which a vibrator is provided;
a wiring portion that is provided at a position, which is different from a position of the vibrator on the first surface, and is connected to the vibrator;
a second substrate that has a second surface that is opposite to the first surface;
a conduction portion that is provided on the second surface, is connected to the wiring portion, and is conductively connected to the vibrator; and
a controller that controls the vibrator,
wherein the shortest distance between the vibrator and the second substrate is longer than the longest distance between the second substrate and a position where the wiring portion is connected to the conduction portion, and
wherein at least one of the wiring portion and the conduction portion includes a resin part and a conductive part covering the resin part.

16. An electronic apparatus comprising:
a first substrate that has a first surface on which a functional element is provided;
a wiring portion that is provided at a position, which is different from a position of the functional element on the first surface, and is conductively connected to the functional element;

a second substrate that has a second surface that is opposite to the first surface; and a conduction portion that is provided on the second surface, is connected to the wiring portion, and is conductively connected to the functional element; and a controller that controls the functional element, wherein the shortest distance between the functional element and the second substrate is longer than the longest distance between the second substrate and a position where the wiring portion is connected to the conduction portion, and wherein at least one of the wiring portion and the conduction portion includes a resin part and a conductive part covering the resin part.

* * * * *